United States Patent
El-Ahmad et al.

(10) Patent No.: US 8,404,848 B2
(45) Date of Patent: Mar. 26, 2013

(54) DERIVATIVES OF IMIDAZO[1,2-A]PYRIDINE-2-CARBOXAMIDES, PREPARATION METHOD THEREOF AND USE OF SAME IN THERAPEUTICS

(75) Inventors: Youssed El-Ahmad, Antony (FR); Anne Olivier, Antony (FR); Jean-Francois Peyronel, Antony (FR)

(73) Assignee: Sanofi, Paris (FR)

( * ) Notice: Subject to any disclaimer, the term of this patent is extended or adjusted under 35 U.S.C. 154(b) by 264 days.

(21) Appl. No.: 12/711,779

(22) Filed: Feb. 24, 2010

(65) Prior Publication Data
US 2010/0168155 A1 Jul. 1, 2010

Related U.S. Application Data

(60) Division of application No. 12/337,007, filed on Dec. 17, 2008, now Pat. No. 7,704,989, which is a continuation of application No. PCT/FR2007/001125, filed on Jul. 3, 2007.

(30) Foreign Application Priority Data

Jul. 3, 2006 (FR) ..................................... 06 06012

(51) Int. Cl.
C07D 471/04 (2006.01)
A61K 31/437 (2006.01)
A61P 25/28 (2006.01)
(52) U.S. Cl. .................... 546/121; 514/210.21; 514/300
(58) Field of Classification Search .................... None
See application file for complete search history.

(56) References Cited

U.S. PATENT DOCUMENTS

| 2004/0204409 | A1 | 10/2004 | Ando et al. | |
| 2009/0149494 | A1* | 6/2009 | Peyronel ...................... | 514/300 |

FOREIGN PATENT DOCUMENTS

| FR | 2638161 | 4/1990 |
| WO | WO 01/74813 | 10/2001 |
| WO | WO 02/080911 | 10/2002 |
| WO | WO 03/059884 | 7/2003 |
| WO | WO 2004/072050 | 8/2004 |
| WO | WO 2005/028444 | 3/2005 |
| WO | WO 2005/044793 | 5/2005 |
| WO | WO 2005/048948 | 6/2005 |
| WO | WO 2006/024834 | 3/2006 |
| WO | WO 2006/067445 | 6/2006 |
| WO | WO 2006/067446 | 6/2006 |

OTHER PUBLICATIONS

U.S. Appl. No. 12/336,989, filed Dec. 17, 2009, Peyronel, et al.
U.S. Appl. No. 12/336,998, filed Dec. 17, 2009, Peyronel, et al.
U.S. Appl. No. 12/337,018, filed Dec. 17, 2009, Peyronel, et al.
Basha, et. al., A Mild, General Method for Conversion of Esthers to Amides, Tetrahedron Letters, No. 48, pp. 4171-4174, (1977), Pergamon Press.
Blache, Y., et. al., Compared Reactivity of 3-, 5-, 6-, and 8-Aminoimidazo[1,2-a]Pyridines in Combes Reaction: Access to Imidiazonaphthyridines and Dipyrido[1,2-a: 3', 2'-d]Imidazole. Heterocycles, vol. 38, No. 7, (1994) pp. 1527-1532.
Grassy, G., et. al., Inhibitory Effects on Platelet Aggregation and Cyclic AMP Phosphodiesterase of Azaindolizine-Type Compounds, Chemometrics and Intelligent Systems, vol. 20, (1993), pp. 71-84.
Kluger, R., et. al., Phosphoenolpyruvamides. Amide-Phosphate Interactions in Analogues of Phosphoenolpyruvate, J. Am. Chem. Soc. (1984), vol. 106, pp. 4017-4020.
Levin. J. I., et. al., An Alternative Procedure for the Aluminum-Mediated Conversion of Esters to Amides, Synthetic Communications, vol. 12, No. 13, pp. 989-993, (1983).
Lombardino, J. G., et. al., Preparation and New Reactions of Imidazo [1,2-a]Pyridines, J. Org. Chem., (1965), vol. 30, No. 7, pp. 2403-2407.
Nahm, S., et. al., N-Methoxy-N-Methylamides as Effective Acylating Agents, Tetrahedron Letters, vol. 22, No. 39, pp. 3815-3818, (1981).
Schmitt. M., et. al., Imidazo[1,2-b]Pyridazines, XXII Some 5-Deaza Analogues. Syntheses of Some 2-Aryl-6-(Chloro, Methoxy, or Unsubstituted)-3-(Variously Substituted)Imidazo[1,2-a]Pyridines, and Their Affinity for Central and Mitochondrial Benzodiazepine Receptors, Aust. J. Chem. (1997), vol. 50, pp. 719-725.
Theuns, J., et. al., A Novel NR4A2 Promoter Variation Associated with Parkinson's Disease Alters Gene Expression, Neurobiology of Aging, vol. 25, (2004-2007), pp. S85.
Wang. Z., et. al., Structure and Function of Nurr1 Identifies a Class of Ligand-Independent Nuclear Receptors, Nature vol. 423, 555-560, (2003).

* cited by examiner

*Primary Examiner* — Kamal Saeed
*Assistant Examiner* — Nyeemah A Grazier
(74) *Attorney, Agent, or Firm* — Scully, Scott, Murphy & Presser, P.C.

(57) ABSTRACT

The present invention is related to a compound of formula (I):

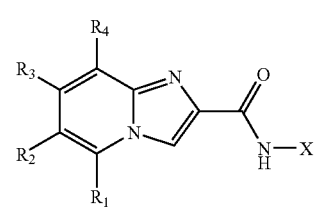

(I)

wherein $R_1$, $R_2$, $R_3$, $R_4$ and X are as defined herein, or an addition salt with an acid thereof, its pharmaceutical composition or use for treating or preventing diseases involving Nurr-1 nuclear receptors, also known as NR4A2, NOT, TINUR, RNR-1 and HZF3.

12 Claims, No Drawings

DERIVATIVES OF IMIDAZO[1,2-A]PYRIDINE-2-CARBOXAMIDES, PREPARATION METHOD THEREOF AND USE OF SAME IN THERAPEUTICS

This application is a Divisional of application Ser. No. 12/337,007, filed Dec. 17, 2008, which is a Continuation of International Application No. PCT/FR2007/001125, filed Jul. 3, 2007, which is incorporated herein by reference in its entirety.

FIELD OF THE INVENTION

The present invention relates to imidazo[1,2-a]pyridine-2-carboxamide derivatives, to their preparation and to their therapeutic application in the treatment or prevention of diseases involving Nurr-1 nuclear receptors, also known as NR4A2, NOT, TINUR, RNR-1 and HZF3.

SUMMARY OF THE INVENTION

A subject matter of the present invention is the compounds corresponding to the formula (I):

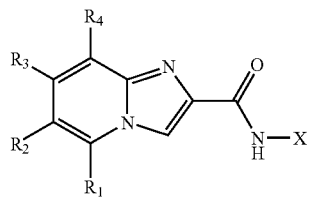

(I)

in which:
X represents one of the following groups:
  a phenyl group optionally substituted by one or more groups chosen, independently of one another, from the following atoms or groups: halogen, $(C_1-C_6)$alkoxy, $(C_1-C_6)$alkyl, $(C_3-C_7)$cycloalkyl$(C_1-C_6)$alkyl, $(C_3-C_7)$cycloalkyl$(C_1-C_6)$alkoxy or NRaRb,
$R_1$ represents a hydrogen atom, a halogen, a $(C_1-C_6)$alkoxy group, a $(C_1-C_6)$alkyl group, a $(C_3-C_7)$cycloalkyl$(C_1-C_6)$alkyl group, a $(C_3-C_7)$cycloalkyl$(C_1-C_6)$-alkoxy group, an amino or an NRcRd group; it being possible for the alkyl and alkoxy groups optionally to be substituted by one or more halogen, hydroxyl, amino, or $(C_1-C_6)$alkoxy group,
$R_2$ represents one of the following groups:
  a hydrogen atom,
  a $(C_1-C_6)$alkyl group optionally substituted by one or more groups chosen, independently of one another, from a hydroxyl, a halogen, an amino, an NRaRb group or a phenyl group,
  a $(C_1-C_6)$alkoxy group optionally substituted by one or more groups chosen, independently of one another, from hydroxyl, halogen, amino or an NRaRb group,
  a $(C_3-C_7)$cycloalkyl$(C_1-C_6)$alkyl group,
  a $(C_3-C_7)$cycloalkyl$(C_1-C_6)$alkoxy group,
  a $(C_2-C_6)$alkenyl group,
  a $(C_2-C_6)$alkynyl group,
  a —CO—$R_5$ group,
  a —CO—NR$_6$R$_7$ group,
  a —CO—O—$R_8$ group,
  a —NR$_9$—CO—R$_{10}$ group,
  a —NR$_{11}$R$_{12}$ group,
  a halogen atom,
  a cyano group,
  a phenyl group optionally substituted by one or more groups chosen, independently of one another, from the following atoms or groups: halogen, $(C_1-C_6)$alkoxy, NRaRb, —CO—$R_5$, —CO—NR$_6$R$_7$, —CO—O—$R_8$, $(C_3-C_7)$-cycloalkyl$(C_1-C_6)$alkyl, $(C_3-C_7)$cycloalkyl $(C_1-C_6)$alkoxy, a $(C_1-C_6)$alkyl group optionally substituted by one or more hydroxyl or NRaRb,
$R_3$ represents a hydrogen atom, a $(C_1-C_6)$alkyl group, a $(C_1-C_6)$alkoxy group or a halogen atom,
$R_4$ represents a hydrogen atom, a $(C_1-C_4)$alkyl group, a $(C_1-C_4)$alkoxy group or a fluorine atom,
$R_5$ represents a hydrogen atom, a phenyl group or a $(C_1-C_6)$ alkyl group,
$R_6$ and $R_7$, which are identical or different, represent a hydrogen atom or a $(C_1-C_6)$alkyl group or form, with the nitrogen atom, a 4- to 7-membered ring optionally including another heteroatom chosen from N, O or S,
$R_8$ represents a $(C_1-C_6)$alkyl group,
$R_9$ and $R_{10}$, which are identical or different, represent a hydrogen atom or a $(C_1-C_6)$alkyl group,
$R_{11}$ and $R_{12}$, which are identical or different, represent a $(C_1-C_6)$alkyl group or form, with the nitrogen atom, a 4- to 7-membered ring optionally including another heteroatom chosen from N, O or S,
Ra and Rb are, independently of one another, hydrogen or $(C_1-C_6)$alkyl or form, with the nitrogen atom, a 4- to 7-membered ring,
Rc is hydrogen and Rd is $(C_1-C_6)$alkyl,
and at least one of the $R_1$, $R_2$, $R_3$ and $R_4$ substituents is other than hydrogen;
and, when $R_3$ is a methyl, X is unsubstituted;
when $R_1$ is a methyl, X is unsubstituted;
when $R_2$ is chlorine, X is not a para-fluorophenyl;
in the form of the base or of an addition salt with an acid.

DETAILED DESCRIPTION OF THE INVENTION

The compounds of formula (I) can comprise one or more asymmetric carbon atoms. They can thus exist in the form of enantiomers or diastereoisomers. These enantiomers or diastereoisomers and their mixtures, including racemic mixtures, come within the invention.

The compounds of formula (I) can exist in the form of bases or of addition salts with acids. Such addition salts come within the invention.

These salts can be prepared with pharmaceutically acceptable acids but the salts of other acids, for example of use in the purification or the isolation of the compounds of formula (I), also come within the invention.

The compounds of formula (I) can also exist in the form of hydrates or solvates, namely in the form of combinations or associations with one or more molecules of water or with a solvent. Such hydrates and solvates also come within the invention.

In the context of the present invention:
  a halogen atom is understood to mean a fluorine, a chlorine, a bromine or an iodine;
  an alkyl group is understood to mean a saturated, linear, branched or cyclic, aliphatic group. Mention may be made, by way of examples, of the methyl, ethyl, propyl, isopropyl, butyl, isobutyl, tert-butyl, cyclopropyl, cyclobutyl, cyclopentyl or cyclohexyl groups, and the like;
  an alkenyl group is understood to mean a mono- or poly-unsaturated, linear or branched, aliphatic group comprising, for example, one or two ethylenic unsaturations;

an alkoxy group is understood to mean an —O-alkyl radical where the alkyl group is as defined above;

an alkynyl group is understood to mean a mono- or polyunsaturated, linear or branched, aliphatic group comprising, for example, one or two acetylenic unsaturations.

Among the compounds of formula (I) which are subject matters of the invention, a first group of compounds is composed of the compounds for which X is a phenyl group.

Among the compounds of formula (I) which are subject matters of the invention, a second group of compounds is composed of the compounds for which $R_1$, $R_3$ and $R_4$ are hydrogen atoms.

Mention may in particular be made, among the compounds of formula (I) which are subject matters of the invention, of the following compounds:

6-Chloro-N-phenylimidazo[1,2-a]pyridine-2-carboxamide
8-Methyl-N-phenylimidazo[1,2-a]pyridine-2-carboxamide
6-(Dimethylamino)-N-phenylimidazo[1,2-a]pyridine-2-carboxamide
6-(1-Hydroxy-1-methylethyl)-N-phenylimidazo[1,2-a]pyridine-2-carboxamide
N-(4-Fluorophenyl)-6-isopropenylimidazo[1,2-a]pyridine-2-carboxamide
6-Chloro-N-(2-chlorophenyl)imidazo[1,2-a]pyridine-2-carboxamide
N,6-Diphenylimidazo[1,2-a]pyridine-2-carboxamide
N-Phenyl-6-vinylimidazo[1,2-a]pyridine-2-carboxamide
6-Ethyl-N-phenylimidazo[1,2-a]pyridine-2-carboxamide
6-Formyl-N-phenylimidazo[1,2-a]pyridine-2-carboxamide
6-Ethynyl-N-phenylimidazo[1,2-a]pyridine-2-carboxamide
6-[3-(1-Hydroxy-1-methylethyl)phenyl]-N-phenylimidazo[1,2-a]pyridine-2-carboxamide
6-[Hydroxy(phenyl)methyl]-N-phenylimidazo[1,2-a]pyridine-2-carboxamide
6-Acetyl-N-phenylimidazo[1,2-a]pyridine-2-carboxamide hydrochloride (1:1)
6-Isopropyl-N-phenylimidazo[1,2-a]pyridine-2-carboxamide
6-(1-Hydroxyethyl)-N-phenylimidazo[1,2-a]pyridine-2-carboxamide
6-Acetamido-N-phenylimidazo[1,2-a]pyridine-2-carboxamide
6-(Dimethylamino)-5-methyl-N-phenylimidazo[1,2-a]pyridine-2-carboxamide
6-Methyl-N-phenylimidazo[1,2-a]pyridine-2-carboxamide
5-Methyl-N-phenylimidazo[1,2-a]pyridine-2-carboxamide
7-Methyl-N-phenylimidazo[1,2-a]pyridine-2-carboxamide
6-Bromo-N-phenylimidazo[1,2-a]pyridine-2-carboxamide
6-Fluoro-N-phenylimidazo[1,2-a]pyridine-2-carboxamide
6,8-Difluoro-N-phenylimidazo[1,2-a]pyridine-2-carboxamide
6-Bromo-5-methyl-N-phenylimidazo[1,2-a]pyridine-2-carboxamide
6-Iodo-N-phenylimidazo[1,2-a]pyridine-2-carboxamide
6-Cyano-N-phenylimidazo[1,2-a]pyridine-2-carboxamide
6-(Hydroxymethyl)-N-phenylimidazo[1,2-a]pyridine-2-carboxamide
6-Methoxy-N-phenylimidazo[1,2-a]pyridine-2-carboxamide
N-(4-Fluorophenyl)-6-(1-hydroxy-1-methylethyl)imidazo[1,2-a]pyridine-2-carboxamide
6-Benzoyl-N-phenylimidazo[1,2-a]pyridine-2-carboxamide
6-Isopropenyl-N-phenylimidazo[1,2-a]pyridine-2-carboxamide
6-Chloro-N-(3-fluorophenyl)imidazo[1,2-a]pyridine-2-carboxamide
6-Chloro-N-(3-chlorophenyl)imidazo[1,2-π]pyridine-2-carboxamide
6-Chloro-N-(3-methoxyphenyl)imidazo[1,2-a]pyridine-2-carboxamide
6-Chloro-N-[4-(dimethylamino)phenyl]imidazo[1,2-a]pyridine-2-carboxamide
6-Chloro-N-(4-chlorophenyl)imidazo[1,2-a]pyridine-2-carboxamide
6-[2-(Hydroxymethyl)phenyl]-N-phenylimidazo[1,2-a]pyridine-2-carboxamide
6-[3-(Hydroxymethyl)phenyl]-N-phenylimidazo[1,2-a]pyridine-2-carboxamide
6-[4-(Hydroxymethyl)phenyl]-N-phenylimidazo[1,2-a]pyridine-2-carboxamide
6-(2-Formylphenyl)-N-phenylimidazo[1,2-a]pyridine-2-carboxamide
6-(3-Formylphenyl)-N-phenylimidazo[1,2-a]pyridine-2-carboxamide
5,6-Dimethyl-N-phenylimidazo[1,2-a]pyridine-2-carboxamide
Methyl 3-[2-(anilinocarbonyl)imidazo[1,2-a]pyridin-6-yl]benzoate
6-(3-Acetylphenyl)-N-phenylimidazo[1,2-a]pyridine-2-carboxamide
6-(3-Fluorophenyl)-N-phenylimidazo[1,2-a]pyridine-2-carboxamide
6-(4-Methylphenyl)-N-phenylimidazo[1,2-a]pyridine-2-carboxamide
6-(3-Methoxyphenyl)-N-phenylimidazo[1,2-a]pyridine-2-carboxamide
6-[3-(Aminomethyl)phenyl]-N-phenylimidazo[1,2-a]pyridine-2-carboxamide
6-(3-Chlorophenyl)-N-phenylimidazo[1,2-a]pyridine-2-carboxamide
6-(3-Carbamoylphenyl)-N-phenylimidazo[1,2-a]pyridine-2-carboxamide
6-[3-(1-Hydroxyethyl)phenyl]-N-phenylimidazo[1,2-a]pyridine-2-carboxamide
6-(3-Methylphenyl)-N-phenylimidazo[1,2-a]pyridine-2-carboxamide
6-(Diethylamino)-N-phenylimidazo[1,2-a]pyridine-2-carboxamide and its hydrochloride (1:1)
6-[3-(Methylcarbamoyl)phenyl]-N-phenylimidazo[1,2-a]pyridine-2-carboxamide and its hydrochloride (1:1)
6-Carbamoyl-N-phenylimidazo[1,2-a]pyridine-2-carboxamide
6-(Dimethylamino)-N-(3-fluorophenyl)imidazo[1,2-a]pyridine-2-carboxamide
N-(2,5-Difluorophenyl)-6-(dimethylamino)imidazo[1,2-a]pyridine-2-carboxamide
N-(2,3-Difluorophenyl)-6-(dimethylamino)imidazo[1,2-a]pyridine-2-carboxamide
6-(Dimethylamino)-N-(2-fluorophenyl)imidazo[1,2-a]pyridine-2-carboxamide
N-(3-Fluorophenyl)-6-[3-(hydroxymethyl)phenyl]imidazo[1,2-a]pyridine-2-carboxamide
N-(3,5-Difluorophenyl)-6-[3-(hydroxymethyl)phenyl]imidazo[1,2-a]pyridine-2-carboxamide
N-(2-Chlorophenyl)-6-[3-(hydroxymethyl)phenyl]imidazo[1,2-a]pyridine-2-carboxamide
6-[3-(Hydroxymethyl)phenyl]-N-(3-methylphenyl)imidazo[1,2-a]pyridine-2-carboxamide
N-(2,5-Difluorophenyl)-6-[3-(hydroxymethyl)phenyl]imidazo[1,2-a]pyridine-2-carboxamide
N-(2,3-Difluorophenyl)-6-[3-(hydroxymethyl)phenyl]imidazo[1,2-a]pyridine-2-carboxamide N-(2-Fluorophenyl)-6-[3-(hydroxymethyl)phenyl]imidazo[1,2-a]pyridine-2-carboxamide
N-(5-Chloro-2-fluorophenyl)-6-[3-(hydroxymethyl)phenyl]imidazo[1,2-a]pyridine-2-carboxamide
6-(Morpholin-4-yl)-N-phenylimidazo[1,2-a]pyridine-2-carboxamide and its hydrochloride (1:1)
6-(Azetidin-1-yl)-N-phenylimidazo[1,2-a]pyridine-2-carboxamide
6-Iodo-5-methyl-N-phenylimidazo[1,2-a]pyridine-2-carboxamide
N-(3,5-Difluorophenyl)-6-iodoimidazo[1,2-a]pyridine-2-carboxamide
N-(3-Chlorophenyl)-6-[3-(hydroxymethyl)phenyl]imidazo[1,2-a]pyridine-2-carboxamide
N-(3,5-Difluorophenyl)-6-(dimethylamino)imidazo[1,2-a]pyridine-2-carboxamide
N-(2-Chlorophenyl)-6-(dimethylamino)imidazo[1,2-a]pyridine-2-carboxamide
6-(Dimethylamino)-N-[3-(trifluoromethoxy)phenyl]imidazo[1,2-a]pyridine-2-carboxamide
N-(3-Chloro-2-fluorophenyl)-6-[3-(hydroxymethyl)phenyl]imidazo[1,2-a]pyridine-2-carboxamide
6-(Dimethylamino)-N-(3-methylphenyl)imidazo[1,2-a]pyridine-2-carboxamide
N-(3-Chlorophenyl)-6-(dimethylamino)imidazo[1,2-a]pyridine-2-carboxamide
N-(5-Chloro-2-fluorophenyl)-6-(dimethylamino)imidazo[1,2-a]pyridine-2-carboxamide
N-(3-Chloro-2-fluorophenyl)-6-(dimethylamino)imidazo[1,2-a]pyridine-2-carboxamide
N-[3-(Difluoromethoxy)phenyl]-6-(dimethylamino)imidazo[1,2-a]pyridine-2-carboxamide
6-(Dimethylamino)-N-[3-(trifluoromethyl)phenyl]imidazo[1,2-a]pyridine-2-carboxamide In accordance with the invention, the compounds of general formula (I) can be prepared according to the process described in Scheme 1.

Route A consists in preparing the 2-aminopyridines of formula (II) according to methods known to a person skilled in the art and in forming the imidazo[1,2-a]pyridine ring by condensation with a 2-oxo-N-arylpropionamide derivative (III), in which Hal represents a chlorine, bromine or iodine atom and X is defined as above, by analogy with the methods described by J-J. Bourguignon et al. in Aust. J. Chem. 1997, 50, 719-725 and by J. G. Lombardino, J. Org. Chem. (1965), 30(7), 2403 for example. The halogenated derivatives of 2-oxo-N-arylpropionamide (III) can be obtained according to the method described by R. Kluger et al. in J. Am. Chem. Soc., (1984) 106(14), 4017.

The second synthetic route, B and C, consists in coupling an imidazopyridine-2-carboxylic acid or one of its derivatives of formula (IV), in which Y is OH or halogen or $(C_1-C_6)$ alkoxy, to an arylamine X—$NH_2$ (VI), in which X is defined as above, according to methods known to a person skilled in the art. Thus, the acid can be converted beforehand to one of its reactive derivatives, such as acid halide, anhydride, mixed anhydride or activated ester, and then reacted with the amine (VI) in the presence of a base, such as diisopropylethylamine, triethylamine or pyridine, in an inert solvent, such as THF, DMF or dichloromethane. The coupling can also be carried out in the presence of a coupling agent, such as CDI, EDCI, HATU or HBTU, under the same conditions without isolation of reactive intermediate. Alternatively, the amine (VI) can be reacted with an ester of the acid of formula (IV) in the presence of a catalyst, such as trimethylaluminum, according to the method of Weinreb, S. et al. (Tet. Lett. (1977), 18, 4171), or zirconium tert-butoxide. The imidazopyridine-2-carboxylic acids and their derivatives of formula (IV) can be obtained by condensing the appropriate 2-aminopyridines with an ester of the 3-halo-2-oxopropionic acid according to the method described by J. G. Lombardino in J. Org. Chem., 30(7), 2403 (1965), and then by deprotecting the ester to give an acid and, if appropriate, converting the acid to one of its derivatives.

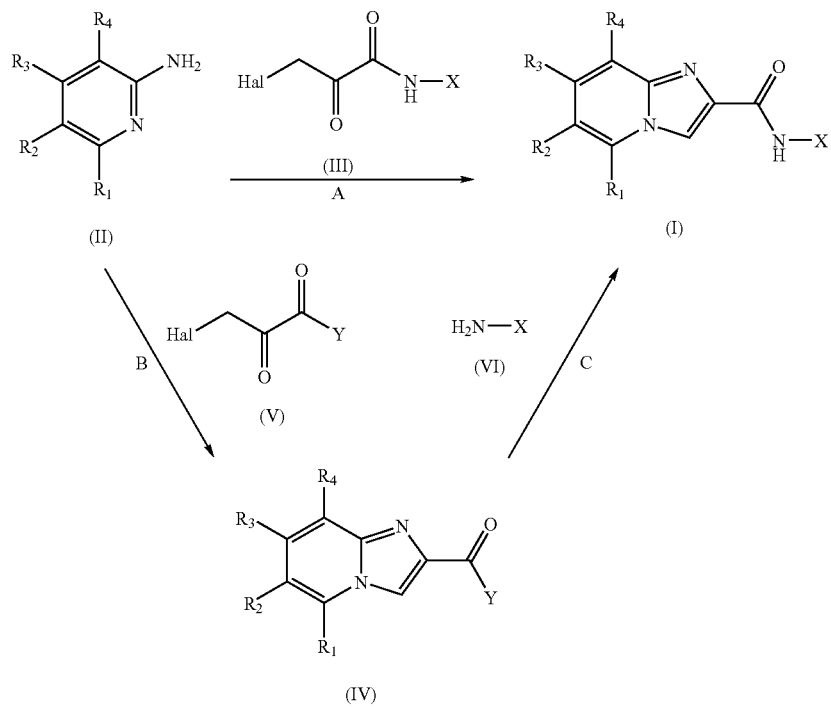

Scheme 1

The products of formula (I) and their precursors of formula (II) or (IV) can be subjected, if desired and necessary, in order to obtain products of formula (I) or to be converted to other products of formula (I), to one or more of the following transformation reactions, in any order:

a) a reaction for the esterification or amidation of an acid functional group,
b) a reaction for the amidation of an amine functional group,
c) a reaction for the hydrolysis of an ester functional group to give an acid functional group,
d) a reaction for the transformation of a hydroxyl functional group to an alkoxy functional group,
e) a reaction for the oxidation of an alcohol functional group to give an aldehyde or ketone functional group,
f) a reaction for the transformation of aldehyde or ketone functional groups to give an alcohol functional group by reduction or by the action of an organometallic compound, such as an organomagnesium compound,
g) a reaction for the transformation of a nitrile radical to give an aldehyde functional group,
h) a reaction for the transformation of a nitrile radical to give a ketone functional group,
i) a reaction for the oxidation of an alkenyl group to give an aldehyde or ketone functional group,
j) a reaction for the olefination of an aldehyde or ketone functional group to give an alkenyl group,
k) a reaction for the dehydration of a hydroxyalkyl group to give an alkenyl group,
l) a reaction for the total or partial hydrogenation of an alkenyl or alkynyl group to give an alkenyl or alkyl group,
m) a reaction for the catalytic coupling of a halogenated derivative and of an organometallic derivative, such as a boron, tin or silicon derivative, in order to introduce an alkyl, alkenyl, alkynyl or aryl substituent,
n) a reaction for the reduction of a nitro group to give a primary amino group,
o) a reaction for the conversion of a primary or secondary amino group to a secondary or tertiary amino group by reductive amination or alkylation,
p) a reaction for the protection of the reactive functional groups,
q) a reaction for the removal of the protective groups which the protected reactive functional groups may carry,
r) a reaction for salification by an inorganic or organic acid or by a base in order to obtain the corresponding salt,
s) a reaction for the resolution of the racemic forms to give enantiomers, said products of formula (I) thus obtained being, if appropriate, in all the possible isomeric forms, racemic, enantiomeric and diastereoisomeric.

In Scheme 1, the starting compounds and the reactants, when their method of preparation is not described, are commercially available or described in the literature or else can be prepared according to methods which are described therein or which are known to a person skilled in the art.

EXAMPLES

The following examples describe the preparation of some compounds in accordance with the invention. These examples are not limiting and serve only to illustrate the present invention. The numbers of the compounds exemplified refer to those given in the table below, in which the chemical structures and the physical properties of some compounds according to the invention are illustrated.

Example 1

6-Chloro-N-phenylimidazo[1,2-a]pyridine-2-carboxamide 1 ml of dimethylformamide is added to a solution of 0.196 g of 6-chloroimidazo[1,2-a]pyridine-2-carboxylic acid in 3 ml of dichloromethane and 0.146 ml of thionyl chloride. The reaction mixture is stirred at ambient temperature for 3 hours. 0.273 ml of aniline is added and the mixture is stirred at ambient temperature for 22 hours. 20 ml of dichloromethane and 10 ml of water are added. After separation by settling, the organic phase is dried over magnesium sulfate, filtered and evaporated to dryness under reduced pressure, and then the residue is purified on a silica column, elution being carried out with dichloromethane. The fractions comprising the product are combined and concentrated to dryness under reduced pressure to give 0.204 g of 6-chloro-N-phenylimidazo[1,2-a]pyridine-2-carboxamide in the form of a white solid.

Example 2

8-Methyl-N-phenylimidazo[1,2-a]pyridine-2-carboxamide 1.67 ml of triethylamine, 1.53 g of 1-(3-dimethylaminopropyl)-3-ethylcarbodiimide hydrochloride and 1.08 g of 1-hydroxybenzotriazole are added to a solution of 0.176 g of 8-methylimidazo[1,2-a]pyridine-2-carboxylic acid in 12 ml of dichloromethane. The reaction mixture is stirred at ambient temperature for 20 minutes. 0.090 ml of aniline is added. The reaction mixture is stirred at ambient temperature for 4 hours. 60 ml of dichloromethane and 30 ml of water are added. After separation by settling, the organic phase is dried over magnesium sulfate, filtered and evaporated to dryness under reduced pressure. After purifying by flash chromatography (silica, eluent dichloromethane/ethyl acetate 98/02 by volume), 0.193 g of 8-methyl-N-phenylimidazo[1,2-a]pyridine-2-carboxamide is obtained in the form of a white solid.

Example 3

6-(Dimethylamino)-N-phenylimidazo[1,2-a]pyridine-2-carboxamide 0.46 ml of a 2M solution of trimethylaluminum in toluene is added dropwise to a solution, cooled to 0° C., of 60.8 µl of aniline in 3 ml of toluene, followed, at 20° C., by the addition of 76 mg of ethyl 6-dimethylaminoimidazo[1,2-a]pyridine-2-carboxylate. The reaction mixture is stirred at ambient temperature for 15 minutes. It is cooled to 0° C. and then 20 ml of a saturated ammonium chloride solution are added. The organic phase is dried over magnesium sulfate, filtered through Celite and evaporated to dryness under reduced pressure. The residue is chromatographed on a silica cartridge, elution being carried out with a mixture of dichloromethane and ethyl acetate. The fractions comprising the product are combined and concentrated to dryness under reduced pressure. The residue obtained is crystallized from methanol to give 36 mg of 6-(dimethylamino)-N-phenylimidazo[1,2-a]pyridine-2-carboxamide in the form of a gray powder.

Example 4

6-(1-Hydroxy-1-methylethyl)-N-phenylimidazo[1,2-a]pyridine-2-carboxamide

A solution of 100 mg of 2-(6-aminopyridin-3-yl)propan-2-ol in 10 ml of 1,2-dimethoxyethane is treated with 190 mg of 3-bromo-2-oxo-N-phenylpropionamide, then stirred at 25° C. for 15 hours and brought to reflux for 3 hours. The reaction mixture is concentrated to dryness under reduced pressure and the residue is taken up in 40 ml of ethyl acetate and 40 ml of a saturated sodium carbonate solution. The aqueous phase is washed twice with 40 ml of ethyl acetate. The combined organic phases are dried and concentrated to dryness under reduced pressure. The residue is chromatographed on a cartridge of 40 g of silica, elution being carried out with dichloromethane and then with mixtures of dichloromethane and methanol, 97/3 and then 95/5. The fractions comprising the expected product are combined and concentrated to dryness to give 63 mg of 6-(1-hydroxy-1-methylethyl)-N-phenylimidazo[1,2-a]pyridine-2-carboxamide in the form of a white solid.

Example 5

N-(4-Fluorophenyl)-6-isopropenylimidazo[1,2-a]pyridine-2-carboxamide

A solution of 110 mg of N-(4-fluorophenyl)-6-(1-hydroxy-1-methylethyl)imidazo[1,2-a]pyridine-2-carboxamide and 3.3 mg of para-toluenesulfonic acid in 5 ml of xylene is heated at reflux for 6 hours and then evaporated to dryness under reduced pressure. The residue is taken up in 200 ml of dichloromethane and 20 ml of water. The organic phase is dried and concentrated, and the residue is purified by chromatography on silica, elution being carried out with a mixture of dichloromethane and ethyl acetate (95/5). The fractions comprising the expected product are combined and concentrated to dryness. The residue is triturated and washed with ethyl ether, filtered off and dried to give 68 mg of N-(4-fluorophenyl)-6-isopropenylimidazo[1,2-a]pyridine-2-carboxamide in the form of a beige solid.

Example 6

6-Chloro-N-(2-chlorophenyl)imidazo[1,2-a]pyridine-2-carboxamide

54 µl of 2-chloroaniline, 211 mg of HATU, 75 mg of 1-hydroxyaminotriazole and 237 µl of N,N-diisopropylethylamine are added to a solution of 100 mg of 6-chloroimidazo[1,2-a]pyridine-2-carboxylic acid in 1 ml of N,N-dimethylformamide. The reaction mixture is heated at 70° C. for 16 hours, diluted with a saturated sodium hydrogencarbonate solution and extracted with ethyl acetate. The combined organic phases are dried and concentrated under reduced pressure. The residue is purified by flash chromatography on silica, elution being carried out with a hexane/ethyl acetate 70/30 mixture to give 62 mg of 6-chloro-N-(2-chlorophenyl)imidazo[1,2-a]pyridine-2-carboxamide in the form of a white solid.

Example 7

N,6-Diphenylimidazo[1,2-a]pyridine-2-carboxamide 0.391 g of 6-iodo-N-phenylimidazo[1,2-a]pyridine-2-carboxamide, 0.237 g of phenylboronic acid, 45 mg of tetrakis(triphenylphosphine)palladium, 4 ml of 2M aqueous sodium carbonate solution, 6 ml of acetonitrile and 6 ml of toluene are charged to a microwave tube. The mixture is heated for 20 minutes in the microwave device adjusted to 150° C. After cooling, the organic phase is separated, dried and evaporated. The residue is taken up in a mixture of dichloromethane and pentane. The solid is filtered off and then purified by triturating from methanol to give 0.22 g of N,6-diphenylimidazo[1,2-a]pyridine-2-carboxamide in the form of an ecru solid.

Example 8

N-Phenyl-6-vinylimidazo[1,2-a]pyridine-2-carboxamide

A mixture of 0.73 g of 6-iodo-N-phenylimidazo[1,2-a]pyridine-2-carboxamide, 209 mg of tetrakis(triphenylphosphine)palladium(0), 587 µl of tributylvinyltin and 17 ml of DMF is heated at 130° C. for 10 minutes in a microwave device and then concentrated to dryness. The residue is taken up in 100 ml of water and extracted with two times 70 ml of ethyl acetate. The combined organic phases are washed with a saturated sodium chloride solution, dried over magnesium sulfate and evaporated to dryness under reduced pressure. The solid is triturated from ethyl acetate, filtered off, washed with ethyl acetate and then with isopropyl ether, and taken up in a mixture of methanol and dichloromethane. The insoluble material is filtered off and washed with methanol. The filtrate is concentrated to dryness under reduced pressure to give 0.29 g of N-phenyl-6-vinylimidazo[1,2-a]pyridine-2-carboxamide in the form of a white solid.

Example 9

6-Ethyl-N-phenylimidazo[1,2-a]pyridine-2-carboxamide

A solution of 60 mg of N-phenyl-6-vinylimidazo[1,2-a]pyridine-2-carboxamide in 15 ml of methanol is hydrogenated at 25° C. for 45 minutes under 1 bar of hydrogen in the presence of 24 mg of 10% palladium-on-charcoal. As the reaction is incomplete, the product is recycled under the same conditions. After filtering, the reaction mixture is concentrated to dryness under reduced pressure. The residue is taken up in 50 ml of ethyl acetate. The organic phase is washed with water, separated by settling, dried and concentrated to dryness under reduced pressure to give 60 mg of 6-ethyl-N-phenylimidazo[1,2-a]pyridine-2-carboxamide in the form of a white solid.

Example 10

6-Formyl-N-phenylimidazo[1,2-a]pyridine-2-carboxamide

A suspension of 150 mg of N-phenyl-6-vinylimidazo[1,2-a]pyridine-2-carboxamide, 232 µl of osmium tetroxide and 167.5 mg of sodium periodate in a mixture of 6 ml of THF, 3 ml of t-butanol and 3 ml of water is stirred at 20° C. for 20 hours and then for a further 48 hours while adding, on 4 occasions, an additional 100 µl of osmium tetroxide and 80 mg of sodium periodate. The reaction mixture is poured into 50 ml of water and extraction is carried out twice with 50 ml of ethyl acetate. The combined organic phases are washed with a saturated aqueous sodium chloride solution, separated by settling, dried and concentrated to dryness under reduced pressure. The residue is chromatographed on silica, elution being carried out with a mixture of cyclohexane and ethyl acetate (gradient from 0 to 50%), to give 100 mg of 6-formyl-N-phenylimidazo[1,2-a]pyridine-2-carboxamide in the form of a white solid.

Example 11

6-Ethynyl-N-phenylimidazo[1,2-a]pyridine-2-carboxamide 0.2 g of 6-iodo-N-phenylimidazo[1,2-a]pyridine-2-carboxamide, 156 µl of trimethylsilylacetylene, 20 mg of dichlorobis(triphenylphosphine)palladium and 2 ml of piperidine are charged to a 20 ml microwave tube. The mixture is heated for 15 minutes in the microwave device adjusted to 130° C. After cooling, the mixture is poured into 50 ml of a saturated aqueous ammonium chloride solution. Extraction is carried out twice with 70 ml of ethyl ether. The combined organic phases are separated by settling, dried and concentrated to dryness under reduced pressure. The residue is taken up in 4 ml of a 1M solution of tetrabutylammonium fluoride in THF and stirred at 25° C. for 16 hours. After evaporating the reaction medium to dryness, the residue is chromatographed on silica, elution being carried out with a mixture of cyclohexane and ethyl acetate (gradient from 0 to 35%), to give 30 mg of 6-ethynyl-N-phenylimidazo[1,2-a]pyridine-2-carboxamide in the form of a beige solid.

Example 12

6-[3-(1-Hydroxy-1-methylethyl)phenyl]-N-phenylimidazo[1,2-a]pyridine-2-carboxamide 781 µl of a 3M solution of methylmagnesium chloride in THF are slowly added to a suspension, placed under an argon atmosphere and cooled to 10° C., of 87 mg of methyl 3-[2-(anilinocarbonyl)imidazo[1,2-a]pyridin-6-yl]benzoate in 5 ml of THF. The mixture is stirred for 16 hours, while allowing the temperature to rise to 20° C., and then poured into 30 ml of a saturated aqueous ammonium chloride solution. Extraction is carried out with 100 ml of ethyl acetate. The organic phase is separated by settling, dried and concentrated to dryness under reduced pressure. The residue is chromatographed on silica, elution being carried out with a mixture of dichloromethane and ethyl acetate (75/25), to give 22 mg of 6-[3-(1-hydroxy-1-methylethyl)phenyl]-N-phenylimidazo[1,2-a]pyridine-2-carboxamide in the form of an ecru solid.

Example 13

6-[Hydroxy(phenyl)methyl]-N-phenylimidazo[1,2-a]pyridine-2-carboxamide 17.4 mg of sodium borohydride are added to a suspension, cooled to 0° C., of 157 mg of 6-benzoyl-N-phenylimidazo[1,2-a]pyridine-2-carboxamide in 10 ml of methanol. The reaction mixture is stirred for 16 hours, while allowing the temperature to rise to 20° C. 20 mg of sodium borohydride are added and the mixture is stirred at 20° C. for a further 1.5 hours. After evaporating to dryness, the residue is taken up in 50 ml of water and 200 ml of ethyl acetate. The organic phase is separated by settling, dried and concentrated to dryness under reduced pressure to give 122 mg of 6-[hydroxy(phenyl)methyl]-N-phenylimidazo[1,2-a]pyridine-2-carboxamide in the form of a white solid.

Example 14

6-Acetyl-N-phenylimidazo[1,2-a]pyridine-2-carboxamide hydrochloride (1:1)

A solution of 90 mg of 6-(1-ethoxyvinyl)-N-phenylimidazo[1,2-a]pyridine-2-carboxamide in 2 ml of dichloromethane is stirred at 20° C. for 18 hours with 1 ml of 2N hydrochloric acid. The solid is filtered off, washed with dichloromethane and then with diisopropyl ether, and dried to give 67 mg of 6-acetyl-N-phenylimidazo[1,2-a]pyridine-2-carboxamide hydrochloride (1:1) in the form of a white solid.

Example 15

6-Isopropyl-N-phenylimidazo[1,2-a]pyridine-2-carboxamide

15. 1 Ethyl 6-isopropylimidazo[1,2-a]pyridine-2-carboxylate

Ethyl 6-isopropylimidazo[1,2-a]pyridine-2-carboxylate is prepared by condensing 2-amino-5-isopropylpyridine (PCT Int. Appl. WO 2005028444) with ethyl 3-bromopyruvate according to the method described by J. G. Lombardino in J. Org. Chem. (1965), 30(7), 2403.

$^1$H NMR spectrum ($d_6$-DMSO, δ in ppm): 1.24 (d, J=7.0 Hz, 6H); 1.32 (t, J=7.0 Hz, 3H); 2.91 (m, 1H); 4.30 (q, J=7.0 Hz, 2H); 7.33 (dd, J=1.5 and 9.5 Hz, 1H); 7.54 (d, J=9.5 Hz, 1H); 8.39 (broad s, 1H); 8.45 (s, 1H).

15. 2 6-Isopropyl-N-phenylimidazo[1,2-a]pyridine-2-carboxamide

A solution of 344 mg of ethyl 6-isopropylimidazo[1,2-a]pyridine-2-carboxylate, 152 mg of aniline, 40 mg of 1-hydroxy-7-azabenzotriazole (HOAt) and 316 mg of zirconium tert-butoxide in 5 ml of toluene is stirred at ambient temperature for 16 hours in a microwave tube. The medium is concentrated to dryness under reduced pressure and the residue is chromatographed on a silica cartridge, elution being carried out with a mixture of dichloromethane and ethyl acetate (50/50). The fractions comprising the expected product are combined and concentrated to dryness under reduced pressure to give 63 mg of 6-isopropyl-N-phenylimidazo[1,2-a]pyridine-2-carboxamide in the form of a white solid.

Example 16

6-[(RS)-1-Hydroxyethyl]-N-phenylimidazo[1,2-a]pyridine

A suspension of 150 mg of 6-formyl-N-phenylimidazo[1,2-a]pyridine-2-carboxamide in 10 ml of tetrahydrofuran is cooled to 5° C. 1.9 ml of a 3M solution of methylmagnesium chloride in tetrahydrofuran are added dropwise. The reaction mixture is stirred at 5° C. for 4 hours, then treated with 20 ml of a saturated ammonium chloride solution, stirred and then diluted with 30 ml of ethyl acetate. The aqueous phase is extracted with ethyl acetate and the combined organic phases are washed with a saturated sodium chloride solution, dried and concentrated to dryness under reduced pressure. After chromatographing on silica, elution being carried out with dichloromethane and then with mixtures of dichloromethane and ethyl acetate (85/15, then 60/40), the fractions comprising the expected product are combined and evaporated to dryness under reduced pressure to give 59 mg of 6-[(RS)-1- hydroxyethyl]-N-phenylimidazo[1,2-a]pyridine-2-carboxamide in the form of a white solid.

Example 17

6-Acetamido-N-phenylimidazo[1,2-a]pyridine-2-carboxamide

17. 1 Ethyl 6-acetamidoimidazo[1,2-a]pyridine-2-carboxylate

A suspension of 0.2 g of ethyl 6-aminoimidazo[1,2-a]pyridine-2-carboxylate (Heterocycles, 38(7), 1527 (1994)) in 1 ml of acetic anhydride is heated at reflux for 45 minutes. The reaction mixture is concentrated under reduced pressure; the residue is taken up in water and basified by addition of a 1N sodium hydroxide solution. The solid is filtered off and dried to give 150 mg of ethyl 6-acetamidoimidazo[1,2-a]pyridine-2-carboxylate in the form of an ecru solid.

$^1$H NMR spectrum (d$_6$-DMSO, δ in ppm): 1.31 (t, J=7.0 Hz, 3H); 2.09 (s, 3H); 4.30 (q, J=7.0 Hz, 2H); 7.24 (dd, J=1.5 and 9.5 Hz, 1H); 7.59 (d, J=9.5 Hz, 1H); 8.60 (s, 1H); 9.23 (broad s, 1H); 10.1 (s, 1H).

Mass spectrum (EI): m/z=246 [M−H]$^−$, m/z=248 [M+H]$^+$.

17. 2 6-Acetamido-N-phenylimidazo[1,2-a]pyridine-2-carboxamide

By carrying out the operation analogously to example 3, 150 mg of ethyl 6-acetamidoimidazo[1,2-a]pyridine-2-carboxylate result in 53 mg of 6-acetamido-N-phenylimidazo[1,2-a]pyridine-2-carboxamide in the form of an ecru solid.

Example 18

6-Dimethylamino-5-methyl-N-phenylimidazo[1,2-a]pyridine-2-carboxamide

18. 1 Ethyl 6-dimethylamino-5-methylimidazo[1,2-a]pyridine-2-carboxylate 1 ml of aqueous formaldehyde solution is added to a solution of 235 mg of ethyl 6-amino-5-methylimidazo[1,2-a]pyridine-2-carboxylate (Heterocycles, 38(7), 1527 (1994)) in 4 ml of formic acid and then the mixture is heated in a bath at 100° C. for 4 hours. After cooling, the reaction mixture is neutralized by addition of a 5N sodium hydroxide solution and extracted with ethyl acetate. The organic phase is dried and evaporated to dryness under reduced pressure. The residue is chromatographed on a silica cartridge, elution being carried out with a mixture of dichloromethane and ethyl acetate (75/25). The fractions comprising the expected product are combined and evaporated to dryness under reduced pressure to give 113 mg of ethyl 6-dimethylamino-5-methylimidazo[1,2-a]pyridine-2-carboxylate in the form of an ecru solid.

$^1$H NMR spectrum (d$_6$-DMSO, δ in ppm): 1.32 (t, J=7.0 Hz, 3H); 2.61 (s, 3H); 2.64 (s, 6H); 4.32 (q, J=7.0 Hz, 2H); 7.49 (d, J=9.5 Hz, 1H); 7.52 (d, J=9.5 Hz, 1H); 8.32 (s, 1H).

Mass spectrum (EI): (LC-MS-DAD-ELSD) m/z=248 [M+H]$^+$, m/z=220 [MH-C$_2$H$_5$]$^+$.

18. 2 6-Dimethylamino-5-methyl-N-phenylimidazo[1,2-a]pyridine-2-carboxamide By carrying out the operation analogously to example 3, 112 mg of ethyl 6-dimethylamino-5-methylimidazo[1,2-a]pyridine-2-carboxylate result in 86 mg of 6-dimethylamino-5-methyl-N-phenylimidazo[1,2-a]pyridine-2-carboxamide in the form of an ecru solid.

The intermediates described below are of use in the preparation of the compounds of the present invention.

2-Aminopyridines of General Formula (II)

2-(6-Aminopyridin-3-yl)propan-2-ol 15 ml of a 3M solution of methylmagnesium chloride in THF are added dropwise to a solution, cooled to 10° C. and under argon, of 0.7 g of methyl 6-aminonicotinate in 65 ml of THF. The reaction mixture is stirred for 15 h, while allowing the temperature to rise to 20° C., and then again cooled in an ice bath. 100 ml of a saturated ammonium chloride solution and then 200 ml of ethyl acetate are slowly added. The organic phase is dried and concentrated to dryness. The residue is taken up in ethyl acetate. The precipitate is filtered off and dried to give 0.4 g of 2-(6-aminopyridin-3-yl)-propan-2-ol in the form of a pale yellow solid.

$^1$H NMR spectrum (d$_6$-DMSO, δ in ppm): 1.36 (s, 6H); 4.82 (s, 1H); 5.67 (broad s, 2H); 6.37 (d, J=9.0 Hz, 1H); 7.42 (dd, J=2.5 and 9.0 Hz, 1H); 7.98 (d, J=2.5 Hz, 1H)

Mass spectrum (EI): m/z 152: [M$^+$.], m/z 137: [M$^+$.]-CH$_3$ (base peak)

5-Dimethylaminopyridine-2-amine

N,N-Dimethyl-6-nitropyridine-3-amine 6 ml of a 2M solution of dimethylamine in tetrahydrofuran are added to a solution of 1 g of 5-bromo-2-nitropyridine in 5 ml of ethanol. The reaction mixture is heated at 140° C. for 2 hours in a microwave device. After cooling, the solid formed is separated off and washed with ethyl ether to give 850 mg of N,N-dimethyl-6-nitropyridine-3-amine in the form of a yellow solid.

$^1$H NMR spectrum (d$_6$-DMSO, δ in ppm): 3.12 (s, 6H); 7.21 (dd, J=3.0 and 9.5 Hz, 1H); 8.02 (d, J=3.0 Hz, 1H); 8.15 (d, J=9.5 Hz, 1H)

Mass spectrum (EI): m/z 167 (base peak): [M$^+$.], m/z 137: [M$^+$.]-NO, m/z 121: [M$^+$.]-NO$_2$.

5-Dimethylaminopyridine-2-amine

The N,N-dimethyl-6-nitropyridine-3-amine obtained above is taken up in 25 ml of ethanol. After addition of 4.8 g of stannous chloride, the reaction mixture is heated at reflux for 30 minutes and then concentrated to dryness. The residue is chromatographed on a column of silica (40-63 μm), elution being carried out with a mixture of dichloromethane and ammoniacal methanol (90/10). The fractions comprising the expected product are combined and concentrated to give 750 mg of 5-dimethylaminopyridine-2-amine in the form of a pasty yellow solid.

$^1$H NMR spectrum (d$_6$-DMSO, δ in ppm): 2.80 (s, 6H); 6.94 (d, J=9.5 Hz, 1H); 7.18 (d, J=3.0 Hz, 1H); 7.32 (broad s, 2H); 7.83 (dd, J=3.0 and 9.5 Hz, 1H)

Mass spectrum (EI): m/z 137 (base peak): [M$^+$.], m/z 122: [M$^+$.]-CH$_3$.

5-(Azetidin-1-yl)pyridine-2-amine

5-(Azetidin-1-yl)-2-nitropyridine 1 g of 5-bromo-2-nitropyridine, 3.5 g of cesium carbonate, 825 mg of bis(diphenylphosphino)ferrocene, 110 mg of palladium acetate and 15 ml of toluene are charged to a microwave tube and then 424 mg of azetidine are added. The tube is stirred and heated in a bath at 105° C., and then left at ambient temperature for 16 h. The reaction mixture is filtered and the solid is rinsed with dichloromethane. The combined filtrates are concentrated to dryness under reduced pressure and the residue is chromatographed on a silica cartridge, elution being carried out with dichloromethane. The fractions comprising the expected product are combined and concentrated to dryness under reduced pressure to give 550 mg of 5-(azetidin-1-yl)-2-nitropyridine in the form of a yellow solid.

5-(Azetidin-1-yl)pyridine-2-amine

The 5-(azetidin-1-yl)-2-nitropyridine obtained above is taken up in 10 ml of ethanol and hydrogenated in the presence of 65 mg of 10% palladium-on-charcoal at 30° C. under a pressure of 1 bar. The reaction mixture is filtered and the filtrate is diluted with 7N ammoniacal methanol and then concentrated to dryness at 30° C. under reduced pressure. The residue is taken up in dichloromethane, an insoluble material is removed and the residue obtained after evaporation to dryness is chromatographed on a silica cartridge, elution being carried out with a mixture of dichloromethane and 7N ammoniacal methanol (90/10). The fractions comprising the expected product are combined and concentrated to give 185 mg of 5-(azetidin-1-yl)pyridine-2-amine in the form of a red oil.

$^1$H NMR spectrum (d$_6$-DMSO, δ in ppm): 2.23 (m, 2H); 3.65 (t, J=7.5 Hz, 4H); 5.12 (broad s, 2H); 6.37 (d, J=9.0 Hz, 1H); 6.68 (dd, J=3.0 and 9.0 Hz, 1H); 7.21 (d, J=3.0 Hz, 1H).

Mass spectrum (EI): m/z=226 [M]$^+$.

Imidazo[1,2-a]pyridine-2-carboxylic acid Derivatives of General Formula (IV)

Ethyl 6-dimethylaminoimidazo[1,2-a]pyridine-2-carboxylate

215 μl of ethyl bromopyruvate are added to a suspension of 0.2 g of 5-dimethylaminopyridine-2-amine in 3 ml of DME. The reaction mixture is stirred at 20° C. for 16 hours, then, after addition of 3 ml of ethanol, for 16 hours at reflux and, finally, concentrated under reduced pressure. The residue is filtered on a cartridge comprising 15 g of silica, elution being carried out with a mixture of dichloromethane and methanol (98/2). The fractions comprising the expected product are combined and washed with a saturated sodium bicarbonate solution. The organic phase is dried and concentrated to dryness under reduced pressure to give 76 mg of ethyl 6-dimethylamino-imidazo[1,2-a]pyridine-2-carboxylate in the form of a green oil used as is in the continuation of the synthesis.

By carrying out the operation in an analogous manner, ethyl 6,8-difluoroimidazo-[1,2-a]pyridine-2-carboxylate is obtained.

$^1$H NMR spectrum (d$_6$-DMSO, δ in ppm): 1.33 (t, J=7.5 Hz, 3H); 4.36 (q, J=7.5 Hz, 2H); 7.66 (ddd, J=2.0, 9.0 and 11.5 Hz, 1H); 8.65 (d, J=3.0 Hz, 1H); 8.70 (m, 1H)

Mass spectrum (EI): m/z=226 [M]$^+$, m/z=181 [M-OC$_2$H$_5$]$^+$, m/z=154 [M-C$_3$H$_4$O$_2$]$^+$ (base peak).

6-(1-Ethoxyvinyl)-N-phenylimidazo[1,2-a]pyridine-2-carboxamide

By carrying out the operation analogously to example 8, tributylvinyltin being replaced with tributyl(1-ethoxyvinyl) tin, 6-(1-ethoxyvinyl)-N-phenylimidazo[1,2-a]pyridine-2-carboxamide is obtained in the form of a beige solid.

$^1$H NMR spectrum (d$_6$-DMSO, δ in ppm): 1.40 (t, J=7.0 Hz, 3H); 3.97 (q, J=7.0 Hz, 2H); 4.46 (d, J=3.0 Hz, 1H); 4.90 (d, J=3.0 Hz, 1H); 7.09 (t, J=8.0 Hz, 1H); 7.34 (broad t, J=8.0 Hz, 2H); 7.61 (d, J=9.5 Hz, 1H); 7.66 (dd, J=2.0 and 9.5 Hz, 1H); 7.89 (broad d, J=8.0 Hz, 2H); 8.57 (s, 1H); 8.83 (broad s, 1H); 10.2 (s, 1H).

The chemical structures (Table 1) and the spectroscopic characteristics (Table 2) of some examples of compounds according to the invention are illustrated in the following tables.

TABLE 1

(I)

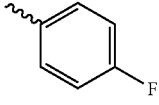

| Ex | R$_1$ | R$_2$ | R$_3$ | R$_4$ | X | salt |
|----|----|----|----|----|----|----|
| 1 | H | Cl | H | H | Ph | |
| 2 | H | H | H | Me | Ph | |
| 3 | H | ~NMe$_2$ | H | H | Ph | |
| 4 | H | ~CMe$_2$OH | H | H | Ph | |
| 5 | H | ~CMe=CH$_2$ | H | H | 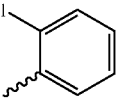 | |
| 6 | H | Cl | H | H | 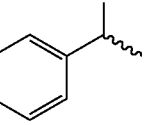 | |
| 7 | H | Ph | H | H | Ph | |
| 8 | H | ~CH=CH$_2$ | H | H | Ph | |
| 9 | H | ~CH$_2$CH$_3$ | H | H | Ph | |
| 10 | H | ~CH=O | H | H | Ph | |
| 11 | H | ~C≡CH | H | H | Ph | |
| 12 | H | 3-(CMe$_2$OH)C$_6$H$_4$- | H | H | Ph | |
| 13 | H | PhCH(OH)- | H | H | Ph | |
| 14 | H | ~COCH$_3$ | H | H | Ph | HCl |
| 15 | H | iPr | H | H | Ph | |
| 16 | H | ~CHOHMe | H | H | Ph | |
| 17 | H | ~NHCOMe | H | H | Ph | |
| 18 | Me | ~NMe$_2$ | H | H | Ph | |
| 19 | H | Me | H | H | Ph | |
| 20 | Me | H | H | H | Ph | |
| 21 | H | H | Me | H | Ph | |
| 22 | H | Br | H | H | Ph | |
| 23 | H | F | H | H | Ph | |
| 24 | H | F | H | F | Ph | |
| 25 | Me | Br | H | H | Ph | |
| 26 | H | I | H | H | Ph | |
| 27 | H | ~CN | H | H | Ph | |
| 28 | H | ~CH$_2$OH | H | H | Ph | |

TABLE 1-continued

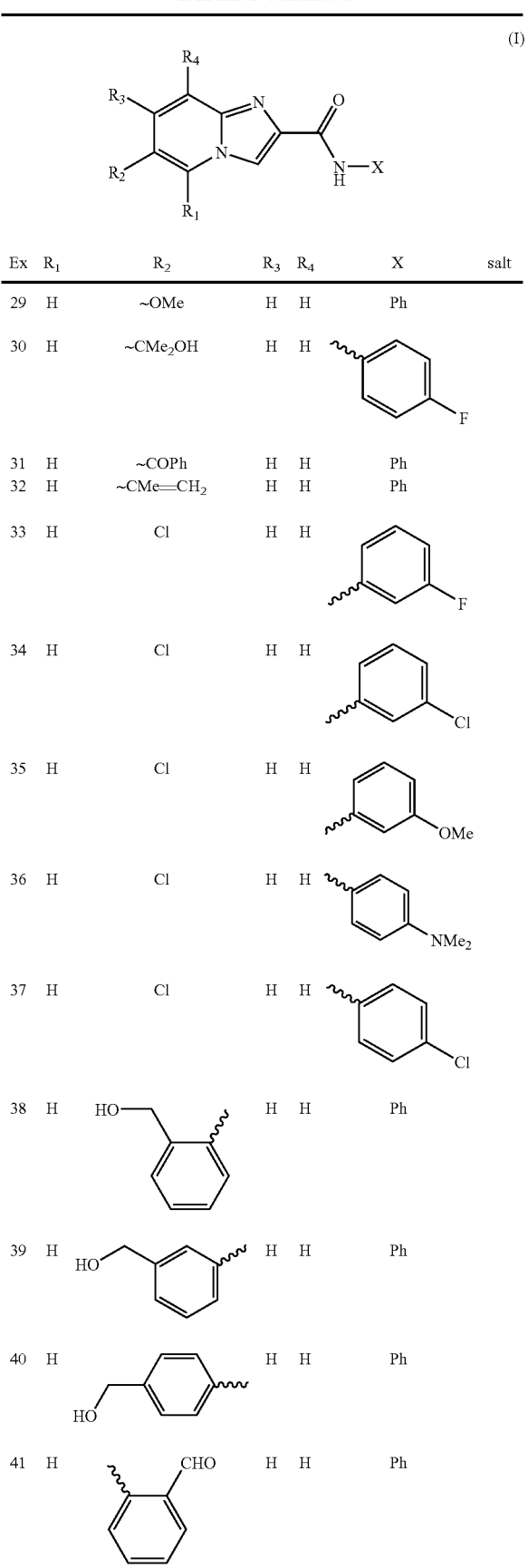

| Ex | R₁ | R₂ | R₃ | R₄ | X | salt |
|---|---|---|---|---|---|---|
| 29 | H | ~OMe | H | H | Ph | |
| 30 | H | ~CMe₂OH | H | H | 4-F-Ph | |
| 31 | H | ~COPh | H | H | Ph | |
| 32 | H | ~CMe=CH₂ | H | H | Ph | |
| 33 | H | Cl | H | H | 3-F-Ph | |
| 34 | H | Cl | H | H | 3-Cl-Ph | |
| 35 | H | Cl | H | H | 3-OMe-Ph | |
| 36 | H | Cl | H | H | 4-NMe₂-Ph | |
| 37 | H | Cl | H | H | 4-Cl-Ph | |
| 38 | H | (HOCH₂-pyridyl) | H | H | Ph | |
| 39 | H | 3-(HOCH₂)-Ph | H | H | Ph | |
| 40 | H | 4-(HOCH₂)-Ph | H | H | Ph | |
| 41 | H | 2-CHO-Ph | H | H | Ph | |

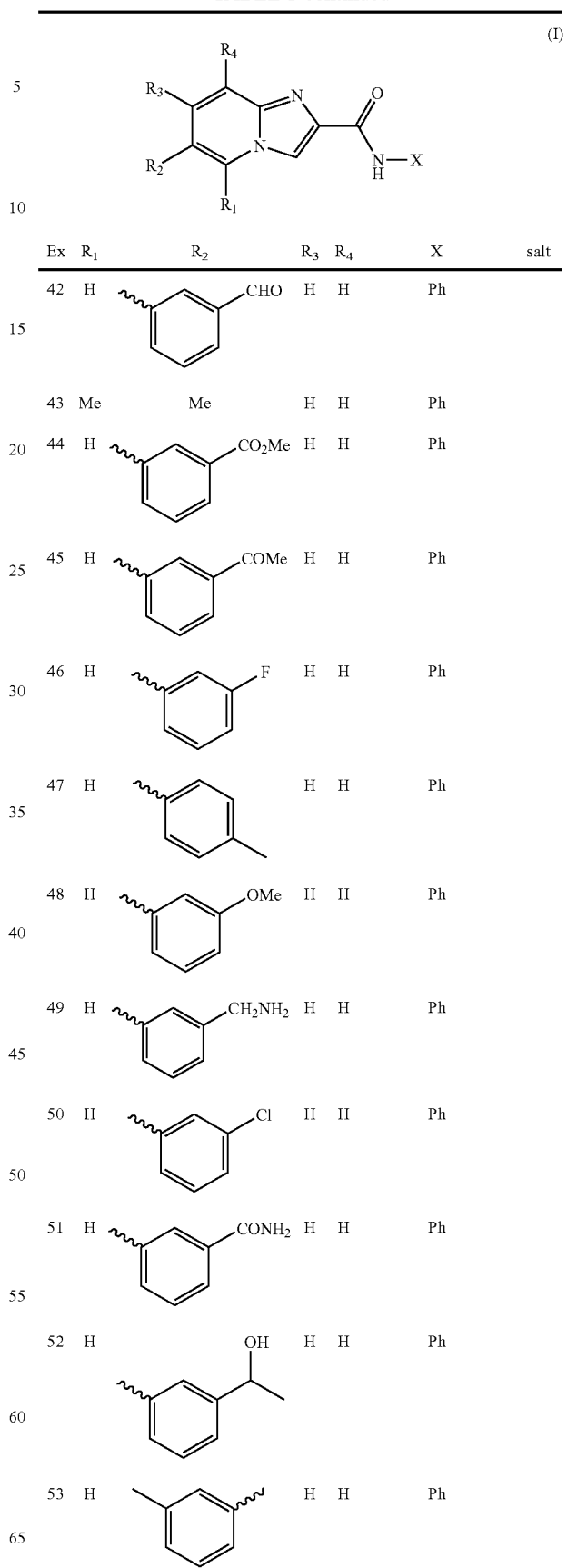

| Ex | R₁ | R₂ | R₃ | R₄ | X | salt |
|---|---|---|---|---|---|---|
| 42 | H | 3-CHO-Ph | H | H | Ph | |
| 43 | Me | Me | H | H | Ph | |
| 44 | H | 3-CO₂Me-Ph | H | H | Ph | |
| 45 | H | 3-COMe-Ph | H | H | Ph | |
| 46 | H | 3-F-Ph | H | H | Ph | |
| 47 | H | 4-Me-Ph | H | H | Ph | |
| 48 | H | 3-OMe-Ph | H | H | Ph | |
| 49 | H | 3-CH₂NH₂-Ph | H | H | Ph | |
| 50 | H | 3-Cl-Ph | H | H | Ph | |
| 51 | H | 3-CONH₂-Ph | H | H | Ph | |
| 52 | H | 3-(CH(OH)Me)-Ph | H | H | Ph | |
| 53 | H | 3-Me-Ph | H | H | Ph | |

TABLE 1-continued (I) Structure: imidazo[1,2-a]pyridine-2-carboxamide with R1 (5-position), R2 (6-position), R3 (7-position), R4 (8-position), and C(O)NH-X group.

| Ex | R₁ | R₂ | R₃ | R₄ | X | salt |
|----|----|----|----|----|---|------|
| 54 | H | ~NEt₂ | H | H | Ph | HCl |
| 55 | H | 3-(N-methylcarbamoyl)phenyl (-NHC(O)- attached to phenyl) | H | H | Ph | HCl |
| 56 | H | ~CONH₂ | H | H | Ph | |
| 57 | H | ~NMe₂ | H | H | 3-fluorophenyl | |
| 58 | H | ~NMe₂ | H | H | 2,5-difluorophenyl | |
| 59 | H | ~NMe₂ | H | H | 2,3-difluorophenyl | |
| 60 | H | ~NMe₂ | H | H | 2-fluorophenyl | |
| 61 | H | 3-(hydroxymethyl)phenyl | H | H | 3-fluorophenyl | |
| 62 | H | 3-(hydroxymethyl)phenyl | H | H | 3,5-difluorophenyl | |
| 63 | H | 3-(hydroxymethyl)phenyl | H | H | 2-chlorophenyl | |
| 64 | H | 3-(hydroxymethyl)phenyl | H | H | 3-methylphenyl | |
| 65 | H | 3-(hydroxymethyl)phenyl | H | H | 2,5-difluorophenyl | |
| 66 | H | 3-(hydroxymethyl)phenyl | H | H | 2,3-difluorophenyl | |
| 67 | H | 3-(hydroxymethyl)phenyl | H | H | 2-fluorophenyl | |
| 68 | H | 3-(hydroxymethyl)phenyl | H | H | 3-chloro-5-fluorophenyl (5-chloro-2-fluorophenyl) | |
| 69 | H | morpholin-4-yl | H | H | Ph | HCl |
| 70 | H | azetidin-1-yl | H | H | Ph | |
| 71 | H | I | Me | H | Ph | |
| 72 | H | I | H | H | 3,5-difluorophenyl | |
| 73 | H | 3-(hydroxymethyl)phenyl | H | H | 3-chlorophenyl | |

TABLE 1-continued

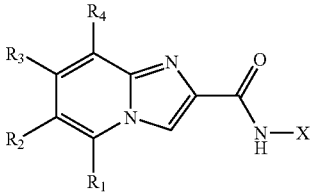
(I)

| Ex | R₁ | R₂ | R₃ | R₄ | X | salt |
|---|---|---|---|---|---|---|
| 74 | H | ~NMe₂ | H | H | 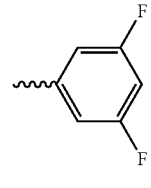 3,5-difluorophenyl | |
| 75 | H | ~NMe₂ | H | H | 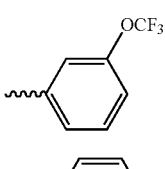 2-chlorophenyl | |
| 76 | H | ~NMe₂ | H | H | 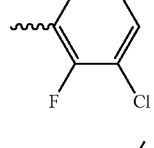 3-OCF₃-phenyl | |
| 77 | H | 3-(hydroxymethyl)phenyl | H | H | 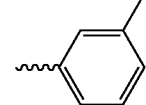 3-fluoro-4-chlorophenyl | |
| 78 | H | ~NMe₂ | H | H | 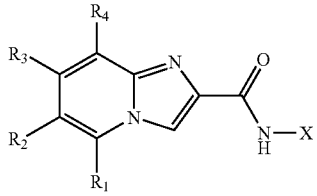 3-methylphenyl | |

TABLE 1-continued

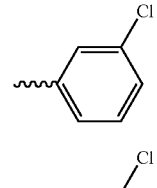
(I)

| Ex | R₁ | R₂ | R₃ | R₄ | X | salt |
|---|---|---|---|---|---|---|
| 79 | H | ~NMe₂ | H | H | 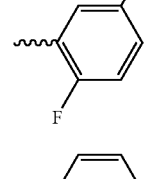 3-chlorophenyl | |
| 80 | H | ~NMe₂ | H | H | 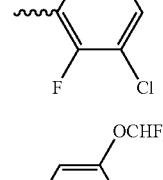 3-chloro-5-fluorophenyl | |
| 81 | H | ~NMe₂ | H | H | 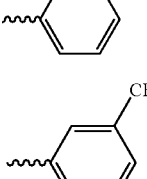 2-fluoro-3-chlorophenyl | |
| 82 | H | ~NMe₂ | H | H | 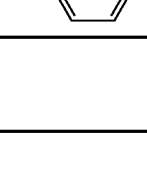 3-OCHF₂-phenyl | |
| 83 | H | ~NMe₂ | H | H | 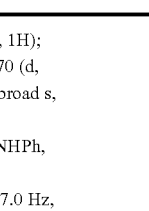 3-CF₃-phenyl | |

TABLE 2

| Ex | Characterizations |
|---|---|
| 1 | ¹H NMR spectrum (d₆-DMSO, δ in ppm): 7.10 (broad t, J = 7.5 Hz, 1H); 7.35 (broad t, J = 7.5 Hz, 2H); 7.45 (dd, J = 2.0 and 9.5 Hz, 1H); 7.70 (d, J = 9.5 Hz, 1H); 7.88 (broad d, J = 8.0 Hz, 2H); 8.48 (s, 1H); 8.90 (broad s, 1H); 10.3 (broad s, 1H)<br>Mass spectrum (EI): m/z 271: [M⁺·], m/z 179 (base peak): [M⁺·] – NHPh, m/z 243: [M⁺·] – [CO]. |
| 2 | ¹H NMR spectrum (d₆-DMSO, δ in ppm): 2.59 (s, 3H); 6.91 (t, J = 7.0 Hz, 1H); 7.10 (broad t, J = 7.5 Hz, 1H); 7.18 (broad d, J = 7.0 Hz, 1H); 7.35 (broad t, J = 7.5 Hz, 2H); 7.86 (broad d, J = 8.0 Hz, 2H); 8.46 (broad d, J = 7.0 Hz, 1H); 8.51 (s, 1H); 9.96 (broad s, 1H)<br>Mass spectrum (EI): m/z 251 (base peak): [M]⁺, m/z 159: [M – NHPh]⁺, m/z 223: [M – CO]⁺. |
| 3 | ¹H NMR spectrum (d₆-DMSO, δ in ppm): 2.86 (s, 6H); 7.07 (broad t, J = 7.5 Hz, 1H); 7.33 (broad t, J = 7.5 Hz, 2H); 7.35 (dd, J = 2.5 and 10.0 Hz, 1H); 7.51 (d, J = 10.0 Hz, 1H); 7.87 (broad d, J = 8.0 Hz, 2H); 7.89 (partially masked d, J = 2.5 Hz, 1H); 8.33 (s, 1H); 10.1 (s, 1H).<br>Mass spectrum (ES): m/z 281 [M + H]⁺.<br>IR spectrum (KBr): 3345; 3140; 2803; 1665; 1643; 1594; 1552; 1523; 1503; 1443; 1310; 1208; 920; 798; 753 & 692 cm⁻¹. |

TABLE 2-continued

| Ex | Characterizations |
|---|---|
| 4 | $^1$H NMR spectrum (d$_6$-DMSO, δ in ppm): 1.49 (s, 6H); 5.32 (s, 1H); 7.09 (t, J = 7.5 Hz, 1H); 7.34 (t, J = 7.5 Hz, 2H); 7.49 (dd, J = 2.0 and 9.5 Hz, 1H); 7.59 (d, J = 9.5 Hz, 1H); 7.89 (d, J = 8.0 Hz, 2H); 8.53 (s, 1H); 8.63 (broad s, 1H); 10.2 (broad s, 1H).<br>IR spectrum (KBr): 3363; 1666; 1597; 1559; 1527; 1504; 1443; 1319; 1204 & 757 cm$^{-1}$<br>Mass spectrum (EI): m/z = 295 [M]$^+$; m/z = 203 [M − NHPh]$^+$ (base peak); m/z = 43 CH$_3$CO$^+$ |
| 5 | $^1$H NMR spectrum (d$_6$-DMSO, δ in ppm): 2.16 (s, 3H); 5.24 (s, 1H); 5.61 (s, 1H); 7.18 (t, J = 9.0 Hz, 2H); 7.61 (d, J = 9.5 Hz, 1H); 7.70 (dd, J = 2.0 and 9.5 Hz, 1H); 7.92 (dd, J = 5.5 and 9.0 Hz, 2H); 8.47 (s, 1H); 8.73 (broad s, 1H); 10.35 (s, 1H).<br>Mass spectrum (LC/MS): m/z 296 [M + H]$^+$ |
| 6 | $^1$H NMR spectrum (d$_6$-DMSO, δ in ppm): 9.91 (s, 1H), 8.91 (s, 1H), 8.53 (s, 1H), 8.31 (d, J = 6.9, 1H), 7.77 (d, J = 9.6, 1H), 7.56 (d, J = 8.0, 1H), 7.49-7.39 (m, 2H), 7.23-7.18 (m, 1H).<br>Mass spectrum (CI): m/z 307: [M + H]$^+$ |
| 7 | $^1$H NMR spectrum (d$_6$-DMSO, δ in ppm): 7.10 (broad t, J = 7.5 Hz, 1H); 7.35 (broad t, J = 7.5 Hz, 2H); 7.44 (broad t, J = 7.5 Hz, 1H); 7.54 (broad t, J = 7.5 Hz, 2H); from 7.71 to 7.77 (m, 4H); 7.91 (broad d, J = 8.0 Hz, 2H); 8.52 (s, 1H); 9.00 (broad s, 1H); 10.3 (broad s, 1H).<br>IR spectrum (KBr): 3360; 1677; 1597; 1556; 1525; 1505; 1489; 1443; 1421; 1314; 1226; 762 & 693 cm$^{-1}$.<br>Mass spectrum (EI): m/z = 313 [M]$^+$, m/z = 221 [M − NHPh]$^+$ (base peak). |
| 8 | $^1$H NMR spectrum (d$_6$-DMSO, δ in ppm): 5.39 (d, J = 11.0 Hz, 1H); 5.92 (d, J = 17.5 Hz, 1H); 6.77 (dd, J = 11.0 and 17.5 Hz, 1H); 7.09 (broad t, J = 7.5 Hz, 1H); 7.34 (broad t, J = 7.5 Hz, 2H); 7.64 (d, J = 9.5 Hz, 1H); 7.70 (dd, J = 2.0 and 9.5 Hz, 1H); 7.89 (broad d, J = 8.0 Hz, 2H); 8.47 (s, 1H); 8.66 (broad s, 1H); 10.2 (s, 1H).<br>Mass spectrum (EI): m/z 263 [M]$^+$. |
| 9 | $^1$H NMR spectrum (d$_6$-DMSO, δ in ppm): 1.24 (t, J = 7.5 Hz, 3H); 2.64 (q, J = 7.5 Hz, 2H); 7.08 (t, J = 8.0 Hz, 1H); from 7.29 to 7.36 (m, 3H); 7.59 (d, J = 9.0 Hz, 1H); 7.89 (broad d, J = 8.0 Hz, 2H); 8.43 (s, 1H); 8.44 (broad s, 1H); 10.2 (s, 1H). |
| 10 | $^1$H NMR spectrum (d$_6$-DMSO, δ in ppm): 7.11 (t, J = 8.0 Hz, 1H); 7.36 (broad t, J = 8.0 Hz, 2H); 7.71 (dd, J = 1.5 and 9.5 Hz, 1H); 7.77 (broad d, J = 9.5 Hz, 1H); 7.90 (broad d, J = 8.0 Hz, 2H); 8.73 (s, 1H); 9.39 (broad s, 1H); 10.0 (s, 1H); 10.35 (broad s, 1H).<br>Mass spectrum (LC/MS): m/z 266 [M + H$^+$] |
| 11 | $^1$H NMR spectrum (d$_6$-DMSO, δ in ppm): 4.37 (s, 1H); 7.09 (t, J = 8.0 Hz, 1H); 7.34 (broad t, J = 8.0 Hz, 2H); 7.39 (broad d, J = 9.5 Hz, 1H); 7.67 (d, J = 9.5 Hz, 1H); 7.89 (broad d, J = 8.0 Hz, 2H); 8.48 (s, 1H); 8.92 (broad s, 1H); 10.3 (s, 1H).<br>Mass spectrum (EI): m/z 261 [M]$^+$ (base peak), m/z = 221 [M − NHPh]$^+$. |
| 12 | $^1$H NMR spectrum (d$_6$-DMSO, δ in ppm): 1.50 (s, 6H); 5.10 (s, 1H); 7.10 (t, J = 8.0 Hz, 1H); 7.35 (broad t, J = 8.0 Hz, 2H); 7.45 (t, J = 8.0 Hz, 1H); 7.54 (m, 2H); 7.75 (m, 2H); 7.82 (broad s, 1H); 7.91 (broad d, J = 8.0 Hz, 2H); 8.54 (s, 1H); 8.98 (broad s, 1H); 10.3 (s, 1H).<br>Mass spectrum (ES): m/z 372 [M + H]$^+$ (base peak) |
| 13 | $^1$H NMR spectrum (d$_6$-DMSO, δ in ppm): 5.78 (s, 1H); 6.20 (s, 1H); 7.08 (t, J = 8.0 Hz, 1H); 7.22 (broad d, J = 9.5 Hz, 1H); 7.26 (broad t, J = 8.0 Hz, 1H); from 7.30 to 7.38 (m, 4H); 7.44 (broad d, J = 8.0 Hz, 2H); 7.56 (d, J = 9.5 Hz, 1H); 7.89 (broad d, J = 8.0 Hz, 2H); 8.56 (s, 1H); 8.70 (broad s, 1H); 10.2 (s, 1H).<br>Mass spectrum (LC/MS): m/z 344 [M + H]$^+$ |
| 14 | $^1$H NMR spectrum (d$_6$-DMSO, δ in ppm): 2.63 (s, 3H); 7.11 (t, J = 7.5 Hz, 1H); 7.36 (broad t, J = 7.5 Hz, 2H); 7.73 (d, J = 10.0 Hz, 1H); 7.85 (dd, J = 2.0 and 10.0 Hz, 1H); 7.89 (broad d, J = 7.5 Hz, 2H); 8.67 (s, 1H); 9.56 (broad s, 1H); 10.4 (s, 1H).<br>Mass spectrum (ES): m/z 280 [M + H]$^+$ (base peak) |
| 15 | $^1$H NMR spectrum (d$_6$-DMSO, δ in ppm): 1.27 (d, J = 7.0 Hz, 6H); 2.95 (m, 1H); 7.09 (t, J = 7.5 Hz, 1H); 7.33 (t, J = 7.5 Hz, 2H); 7.38 (dd, J = 1.5 and 9.5 Hz, 1H); 7.60 (d, J = 9.5 Hz, 1H); 7.90 (d, J = 7.5 Hz, 2H); 8.43 (s, 1H); 8.47 (broad s, 1H); 10.2 (s, 1H).<br>Mass spectrum (LC-MS-DAD-ELSD): m/z 280 [M + H]$^+$ |
| 16 | $^1$H NMR spectrum (d$_6$-DMSO, δ in ppm): 1.40 (d, J = 6.5 Hz, 3H); 4.79 (m, 1H); 5.42 (d, J = 4.0 Hz, 1H); 7.09 (t, J = 8.0 Hz, 1H); 7.33 (t, J = 8.0 Hz, 2H); 7.39 (broad d, J = 9.5 Hz, 1H); 7.61 (d, J = 9.5 Hz, 1H); 7.89 (d, J = 8.0 Hz, 2H); 8.51 (s, 1H); 8.56 (broad s, 1H); 10.2 (s, 1H).<br>Mass spectrum (LC-MS-DAD-ELSD): m/z 282 [M + H]$^+$ |
| 17 | $^1$H NMR spectrum (d$_6$-DMSO, δ in ppm): 2.10 (s, 3H); 7.09 (t, J = 7.5 Hz, 1H); 7.30 (dd, J = 1.5 and 9.5 Hz, 1H); 7.33 (t, J = 7.5 Hz, 2H); 7.63 (d, J = 9.5 Hz, 1H); 7.88 (d, J = 7.5 Hz, 2H); 8.58 (s, 1H); 9.29 (broad s, 1H); 10.15 (s, 1H).<br>Mass spectrum (LC-MS-DAD-ELSD): m/z 295 [M + H]$^+$ |

TABLE 2-continued

| Ex | Characterizations |
|---|---|
| 18 | $^1$H NMR spectrum (d$_6$-DMSO, δ in ppm): 2.65 (s, 3H); 2.67 (s, 6H); 7.09 (t, J = 7.5 Hz, 1H); 7.34 (t, J = 7.5 Hz, 2H); 7.52 (d, J = 9.5 Hz, 1H); 7.58 (d, J = 9.5 Hz, 1H); 7.90 (d, J = 7.5 Hz, 2H); 8.34 (s, 1H); 10.2 (s, 1H). Mass spectrum (LC-MS-DAD-ELSD): m/z 295 [M + H]$^+$, m/z 220 [MH − Ph]$^+$, m/z 202 [MH − NHPh]$^+$. |
| 19 | $^1$H NMR spectrum (d$_6$-DMSO, δ in ppm): 2.30 (s, 3H); 7.08 (broad t, J = 7.5 Hz, 1H); 7.25 (dd, J = 2.0 and 9.5 Hz, 1H); 7.34 (broad t, J = 7.5 Hz, 2H); 7.57 (d, J = 9.5 Hz, 1H); 7.89 (broad d, J = 8.0 Hz, 2H); 8.42 (broad s, 2H); 10.2 (broad s, 1H) Mass spectrum (EI): m/z 251 [M$^{+\cdot}$], m/z 159 (base peak): [M − NHPh]$^+$, m/z 223: [M − CO]$^+$. |
| 20 | $^1$H NMR spectrum (d$_6$-DMSO, δ in ppm): 2.68 (s, 3H); 6.90 (broad d, J = 7.0 Hz, 1H); 7.09 (broad t, J = 7.5 Hz, 1H); from 7.30 to 7.40 (m, 3H); 7.57 (broad d, J = 9.0 Hz, 1H); 7.91 (broad d, J = 8.0 Hz, 2H); 8.41 (broad s, 1H); 10.3 (broad s, 1H) Mass spectrum (EI): m/z 251 (base peak): [M$^{+\cdot}$], m/z 159: [M$^{+\cdot}$] − NHPh. |
| 21 | $^1$H NMR spectrum (d$_6$-DMSO, δ in ppm): 2.39 (s, 3H); 6.87 (dd, J = 1.5 and 7.0 Hz, 1H); 7.08 (broad t, J = 7.5 Hz, 1H); 7.33 (broad t, J = 7.5 Hz, 2H); 7.41 (broad s, 1H); 7.88 (broad d, J = 8.0 Hz, 2H); 8.42 (s, 1H); 8.49 (broad d, J = 7.0 Hz, 1H); 10.15 (broad s, 1H). Mass spectrum (EI): m/z 251 (base peak): [M]$^+$, m/z 159: [M − NHPh]$^+$, m/z 223: [M − CO]$^+$. |
| 22 | $^1$H NMR spectrum (d$_6$-DMSO, δ in ppm): 7.10 (broad t, J = 7.5 Hz, 1H); 7.35 (broad t, J = 7.5 Hz, 2H); 7.51 (dd, J = 2.0 and 9.5 Hz, 1H); 7.65 (d, J = 9.5 Hz, 1H); 7.88 (broad d, J = 8.0 Hz, 2H); 8.47 (s, 1H); 8.99 (d, J = 2.0 Hz, 1H); 10.3 (broad s, 1H) Mass spectrum (EI): m/z 315 (base peak): [M]$^+$, m/z 223: [M − NHPh]$^+$, m/z 287: [M − CO]$^+$. |
| 23 | $^1$H NMR spectrum (d$_6$-DMSO, δ in ppm): 7.10 (broad t, J = 7.5 Hz, 1H); 7.34 (broad t, J = 7.5 Hz, 2H); 7.50 (ddd, J = 2.5, 8.0 and 10.0 Hz, 1H); 7.73 (dd, J = 5.0 and 10.0 Hz, 1H); 7.89 (broad d, J = 8.5 Hz, 2H); 8.50 (broad s, 1H); 8.83 (broad dd, J = 2.5 and 4.5 Hz, 1H); 10.25 (broad s, 1H). Mass spectrum (EI): m/z 255 (base peak): [M]$^+$, m/z 163: [M − NHPh]$^+$, m/z 227: [M − CO]$^+$. IR spectrum (KBr): 3384; 3136; 1674; 1559; 1504; 1222; 1167; 797; 756; 687 cm$^{-1}$. |
| 24 | $^1$H NMR spectrum (d$_6$-DMSO, δ in ppm): 7.10 (broad t, J = 7.5 Hz, 1H); 7.35 (broad t, J = 7.5 Hz, 2H); 7.69 (ddd, J = 2.0, 9.0 and 11.5 Hz, 1H); 7.88 (broad d, J = 8.0 Hz, 2H); 8.63 (d, J = 3.0 Hz, 1H); 8.77 (m, 1H); 10.3 (broad s, 1H) Mass spectrum (EI): m/z 273: [M]$^+$, m/z 181 (base peak): [M − NHPh]$^+$, m/z 245: [M − CO]$^+$. IR spectrum (KBr): 3366; 3149; 1676; 1596; 1559; 1503; 1437; 1335; 1224; 1142; 1109; 883; 851 & 767 cm$^{-1}$. |
| 25 | $^1$H NMR spectrum (d$_6$-DMSO, δ in ppm): 2.81 (s, 3H); 7.10 (broad t, J = 7.5 Hz, 1H); 7.35 (broad t, J = 7.5 Hz, 2H); 7.53 (broad d, J = 9.5 Hz, 1H); 7.58 (d, J = 9.5 Hz, 1H); 7.89 (broad d, J = 8.0 Hz, 2H); 8.53 (s, 1H); 10.3 (broad s, 1H) Mass spectrum (EI): m/z 329 (base peak): [M$^{+\cdot}$], m/z 237: [M − NHPh]$^+$, m/z 301: [M − CO]$^+$. |
| 26 | $^1$H NMR spectrum (d$_6$-DMSO, δ in ppm): 7.09 (t, J = 7.5 Hz, 1H); 7.34 (t, J = 7.5 Hz, 2H); 7.51 (d, J = 9.5 Hz, 1H); 7.57 (dd, J = 1.5 and 9.5 Hz, 1H); 7.88 (d, J = 8.0 Hz, 2H); 8.42 (s, 1H); 9.02 (broad s, 1H); 10.25 (s, 1H). IR spectrum (KBr): 3380; 1674; 1596; 1557; 1523; 1442; 1314 & 790 cm$^{-1}$ Mass spectrum (EI): m/z 363 [M]$^+$ (base peak), m/z = 271 [M − C$_6$H$_6$N]$^+$, m/z = 144 [m/z = 271-I]$^+$. |
| 27 | $^1$H NMR spectrum (d$_6$-DMSO, δ in ppm): 7.11 (t, J = 7.5 Hz, 1H); 7.35 (t, J = 7.5 Hz, 2H); 7.65 (dd, J = 2.0 and 9.5 Hz, 1H); 7.81 (d, J = 9.5 Hz, 1H); 7.89 (d, J = 8.0 Hz, 2H); 8.58 (s, 1H); 9.41 (broad s, 1H); 10.4 (broad s, 1H) IR spectrum (KBr): 3364; 2234; 1671; 1599; 1560; 1527; 1504; 1433 & 748 cm$^{-1}$ Mass spectrum (EI): m/z = 262 [M]$^+$ (base peak), m/z = 170 [M − NHPh]$^+$, m/z = 143 [m/z = 170-HCN]$^+$. |
| 28 | $^1$H NMR spectrum (d$_6$-DMSO, δ in ppm): 4.54 (d, J = 5.5 Hz, 2H); 5.43 (t, J = 5.5 Hz, 1H); 7.09 (t, J = 8.0 Hz, 1H); 7.34 (m, 3H); 7.62 (d, J = 9.5 Hz, 1H); 7.89 (broad d, J = 8.0 Hz, 2H); 8.53 (s, 1H); 8.54 (broad s, 1H); 10.2 (s, 1H). |
| 29 | $^1$H NMR spectrum (d$_6$-DMSO, δ in ppm): 3.82 (s, 3H); 7.08 (broad t, J = 7.5 Hz, 1H); 7.19 (dd, J = 2.5 and 9.5 Hz, 1H); 7.34 (broad t, J = 7.5 Hz, 2H); 7.58 (d, J = 9.5 Hz, 1H); 7.88 (broad d, J = 8.0 Hz, 2H); 8.32 (d, J = 2.5 Hz, 1H); 8.41 (s, 1H); 10.15 (s, 1H). Mass spectrum (ES): m/z 268 [M + H]$^+$. IR spectrum (KBr): 3344; 3140; 2841; 1664; 1594; 1552; 1539; 1505; 1446; 1319; 1215; 1022; 986; 801; 762 & 692 cm$^{-1}$ |

TABLE 2-continued

| Ex | Characterizations |
|---|---|
| 30 | $^1$H NMR spectrum (d$_6$-DMSO, δ in ppm): 1.49 (s, 6H); 5.32 (s, 1H); 7.17 (t, J = 9.0 Hz, 1H); 7.49 (dd, J = 2.0 and 9.0 Hz, 2H); 7.58 (d, J = 9.0 Hz, 1H); 7.92 (dd, J = 5.0 and 9.0 Hz, 2H); 8.52 (s, 1H); 8.62 (broad s, 1H); 10.35 (s, 1H). <br> Mass spectrum (ES): m/z = 203 [M − C$_6$H$_5$FN]$^+$ (base peak), m/z = 313 [M]$^+$ |
| 31 | $^1$H NMR spectrum (d$_6$-DMSO, δ in ppm): 7.10 (t, J = 8.0 Hz, 1H); 7.35 (broad t, J = 8.0 Hz, 2H); 7.62 (t, J = 8.0 Hz, 2H); from 7.71 to 7.82 (m, 3H); 7.88 (broad d, J = 8.0 Hz, 2H); 7.91 (broad d, J = 8.0 Hz, 2H); 8.65 (s, 1H); 9.17 (broad s, 1H); 10.35 (s, 1H). |
| 32 | $^1$H NMR spectrum (d$_6$-DMSO, δ in ppm): 2.16 (s, 3H); 5.24 (broad s, 1H); 5.62 (s, 1H); 7.09 (broad t, J = 7.5 Hz, 1H); 7.34 (broad t, J = 7.5 Hz, 2H); 7.61 (broad d, J = 9.5 Hz, 1H); 7.70 (dd, J = 2.0 and 9.5 Hz, 1H); 7.88 (broad d, J = 8.0 Hz, 2H); 8.48 (s, 1H); 8.73 (broad s, 1H); 10.2 (broad s, 1H). <br> IR spectrum (KBr): 3331; 1673; 1594; 1533; 1524; 1504; 1443; 1428; 1314; 1207; 756 & 692 cm$^{-1}$. <br> Mass spectrum (EI): m/z = 277 [M]$^+$, m/z = 185 [M − NHPh]$^+$ (base peak). |
| 33 | $^1$H NMR spectrum (d$_6$-DMSO, δ in ppm): 6.92 (dt, J = 2.0 and 8.5 Hz, 1H); 7.37 (m, 1H); 7.45 (dd, J = 2.0 and 10.0 Hz, 1H); from 7.68 to 7.78 (m, 2H); 7.86 (td, J = 2.0 and 11.5 Hz, 1H); 8.50 (s, 1H); 8.92 (broad s, 1H); 10.6 (s, 1H). <br> Mass spectrum (CI): m/z 289 [M$^+$] |
| 34 | $^1$H NMR spectrum (d$_6$-DMSO, δ in ppm): 7.15 (broad d, J = 8.0 Hz, 1H); 7.37 (t, J = 8.0 Hz, 1H); 7.46 (dd, J = 2.0 and 9.5 Hz, 1H); 7.71 (d, J = 9.5 Hz, 1H); 7.85 (broad d, J = 8.0 Hz, 1H); 8.10 (broad s, 1H); 8.50 (s, 1H); 8.91 (broad s, 1H); 10.6 (s, 1H). <br> Mass spectrum (CI): m/z 305 [M]$^+$ |
| 35 | $^1$H NMR spectrum (d$_6$-DMSO, δ in ppm): 3.76 (s, 3H); 6.68 (dd, J = 2.5 and 8.5 Hz, 1H); 7.24 (t, J = 8.5 Hz, 1H); 7.45 (dd, J = 2.0 and 9.5 Hz, 1H); 7.49 (broad d, J = 8.5 Hz, 1H); 7.59 (t, J = 2.5 Hz, 1H); 7.70 (d, J = 9.5 Hz, 1H); 8.47 (s, 1H); 8.91 (broad s, 1H); 10.25 (s, 1H). <br> Mass spectrum (CI): m/z 301 [M]$^+$ |
| 36 | $^1$H NMR spectrum (d$_6$-DMSO, δ in ppm): 2.87 (s, 6H); 6.72 (d, J = 9.0 Hz, 2H); 7.43 (dd, J = 2.0 and 9.5 Hz, 1H); 7.67 (d, J = 9.0 Hz, 2H); 7.69 (d, J = 9.5 Hz, 1H); 8.42 (s, 1H); 8.91 (broad s, 1H); 10.0 (s, 1H). <br> Mass spectrum (CI): m/z 315 [M + H]$^+$ |
| 37 | $^1$H NMR spectrum (d$_6$-DMSO, δ in ppm): 7.40 (d, J = 9.0 Hz, 2H); 7.45 (broad d, J = 10.0 Hz, 1H); 7.71 (d, J = 10.0 Hz, 1H); 7.95 (d, J = 9.0 Hz, 2H); 8.49 (s, 1H); 8.91 (broad s, 1H); 10.5 (s, 1H). <br> Mass spectrum (CI): m/z 305 [M]$^+$ |
| 38 | $^1$H NMR spectrum (d$_6$-DMSO, δ in ppm): 4.47 (d, J = 5.5 Hz, 2H); 5.23 (t, J = 5.5 Hz, 1H); 7.10 (t, J = 7.5 Hz, 1H); from 7.31 to 7.50 (m, 6H); 7.60 (d, J = 8.0 Hz, 1H); 7.70 (d, J = 9.5 Hz, 1H); 7.92 (d, J = 8.0 Hz, 2H); 8.53 (s, 1H); 8.66 (s, 1H); 10.3 (broad s, 1H). <br> IR spectrum (KBr): 3374; 1668; 1602; 1560; 1526; 1502; 1444; 1420; 1317; 754 & 691 cm$^{-1}$ <br> Mass spectrum (ES): m/z = 344 [M + H]$^+$ (base peak). |
| 39 | $^1$H NMR spectrum (d$_6$-DMSO, δ in ppm): 4.61 (d, J = 5.5 Hz, 2H); 5.29 (broad t, J = 5.5 Hz, 1H); 7.10 (broad t, J = 7.5 Hz, 1H); from 7.31 to 7.41 (m, 3H); 7.48 (t, J = 8.0 Hz, 1H); 7.60 (broad d, J = 8.0 Hz, 1H); 7.68 (broad s, 1H); 7.74 (broad s, 2H); 7.91 (broad d, J = 8.0 Hz, 2H); 8.54 (s, 1H); 8.99 (broad s, 1H); 10.25 (broad s, 1H). <br> IR spectrum (KBr): 3373; 1667; 1602; 1560; 1535; 1503; 1443; 1413; 1320; 1208 & 755 cm$^{-1}$. <br> Mass spectrum (ES): m/z = 344 [M + H]$^+$ (base peak). |
| 40 | $^1$H NMR spectrum (d$_6$-DMSO, δ in ppm): 4.57 (d, J = 5.5 Hz, 2H); 5.25 (broad t, J = 5.5 Hz, 1H); 7.10 (broad t, J = 7.5 Hz, 1H); 7.35 (broad t, J = 7.5 Hz, 2H); 7.47 (d, J = 8.5 Hz, 2H); 7.70 (d, J = 8.5 Hz, 2H); 7.74 (broad s, 2H); 7.91 (broad d, J = 8.5 Hz, 2H); 8.51 (s, 1H); 8.99 (broad s, 1H); 10.25 (broad s, 1H). <br> IR spectrum (KBr): 3353; 1664; 1599; 1558; 1529; 1500; 1443; 1432; 1316; 1244; 802 & 755 cm$^{-1}$. <br> Mass spectrum (ES): m/z = 344 [M + H]$^+$ (base peak). |
| 41 | $^1$H NMR spectrum (d$_6$-DMSO, δ in ppm): 7.10 (broad t, J = 7.5 Hz, 1H); 7.35 (broad t, J = 7.5 Hz, 2H); 7.52 (dd, J = 2.0 and 9.5 Hz, 1H); 7.64 (broad d, J = 7.5 Hz, 1H); 7.68 (broad t, J = 7.5 Hz, 1H); 7.75 (d, J = 9.5 Hz, 1H); 7.82 (broad t, J = 7.5 Hz, 1H); 7.92 (broad d, J = 8.0 Hz, 2H); 8.01 (broad d, J = 8.0 Hz, 1H); 8.54 (s, 1H); 8.78 (broad s, 1H); 10.5 (s, 1H); 10.3 (broad s, 1H). <br> Mass spectrum (ES): m/z 342 [M + H]$^+$. |
| 42 | $^1$H NMR spectrum (d$_6$-DMSO, δ in ppm): 7.10 (broad t, J = 7.5 Hz, 1H); 7.35 (broad t, J = 7.5 Hz, 2H); from 7.74 to 7.86 (m, 3H); 7.91 (broad d, J = 8.0 Hz, 2H); 7.98 (broad d, J = 7.5 Hz, 1H); 8.10 (broad d, J = 8.0 Hz, 1H); 8.28 (broad s, 1H); 8.54 (s, 1H); 9.13 (broad s, 1H); 10.15 (s, 1H); 10.3 (broad s, 1H). <br> IR spectrum (KBr): 3353; 3155; 2858; 2735; 1695; 1670; 1599; 1556; 1526; 1504; 1441; 1315; 1207; 797; 745 & 690 cm$^{-1}$. <br> Mass spectrum (EI): m/z 341 [M]$^+$. |

TABLE 2-continued

| Ex | Characterizations |
|---|---|
| 43 | $^1$H NMR spectrum (d$_6$-DMSO, δ in ppm): 2.34 (s, 3H); 2.61 (s, 3H); 7.09 (broad t, J = 7.5 Hz, 1H); 7.29 (d, J = 9.5 Hz, 1H); 7.34 (broad t, J = 7.5 Hz, 2H); 7.49 (d, J = 9.5 Hz, 1H); 7.90 (broad d, J = 8.0 Hz, 2H); 8.37 (s, 1H); 10.2 (s, 1H).<br>Mass spectrum (EI): m/z 265 (base peak): [M$^{+\cdot}$], m/z 173: [M$^{+\cdot}$] − NHPh, m/z 237: [M$^+$] − [CO]. |
| 44 | $^1$H NMR spectrum (d$_6$-DMSO, δ in ppm): 3.92 (s, 3H); 7.10 (t, J = 8.0 Hz, 1H); 7.35 (broad t, J = 8.0 Hz, 2H); 7.70 (t, J = 7.5 Hz, 1H); from 7.75 to 7.82 (m, 2H); 7.91 (broad d, J = 8.0 Hz, 2H); from 8.00 to 8.06 (m, 2H); 8.28 (t, J = 2.0 Hz, 1H); 8.54 (s, 1H); 9.10 (broad s, 1H); 10.3 (s, 1H).<br>Mass spectrum (ES): m/z = 372 [M + H]$^+$ (base peak) |
| 45 | $^1$H NMR spectrum (d$_6$-DMSO, δ in ppm): 2.68 (s, 3H); 7.10 (t, J = 7.5 Hz, 1H); 7.36 (broad t, J = 7.5 Hz, 2H); 7.70 (t, J = 7.5 Hz, 1H); 7.77 (d, J = 9.5 Hz, 1H); 7.83 (dd, J = 2.0 and 9.5 Hz, 1H); 7.91 (broad d, J = 7.5 Hz, 2H); 8.02 (broad d, J = 7.5 Hz, 2H); 8.28 (t, J = 2.0 Hz, 1H); 8.54 (s, 1H); 9.11 (broad s, 1H); 10.25 (s, 1H).<br>Mass spectrum (ES): m/z = 356 [M + H]$^+$ (base peak) |
| 46 | $^1$H NMR spectrum (d$_6$-DMSO, δ in ppm): 7.10 (t, J = 8.0 Hz, 1H); 7.27 (m, 1H); 7.35 (broad t, J = 8.0 Hz, 2H); from 7.54 to 7.65 (m, 3H); 7.75 (d, J = 9.0 Hz, 1H); 7.78 (dd, J = 2.0 and 9.0 Hz, 1H); 7.91 (broad d, J = 8.0 Hz, 2H); 8.50 (s, 1H); 9.07 (broad s, 1H); 10.3 (s, 1H).<br>Mass spectrum (EI): m/z 239: [M − C$_6$H$_6$N$^+$] (base peak), m/z 331: [M$^+$] |
| 47 | $^1$H NMR spectrum (d$_6$-DMSO, δ in ppm): 2.37 (s, 3H); 7.10 (t, J = 8.0 Hz, 1H); from 7.31 to 7.38 (m, 4H); 7.63 (d, J = 8.0 Hz, 2H); 7.73 (d, J = 2.0 Hz, 1H); 7.91 (broad d, J = 8.0 Hz, 2H); 8.50 (s, 1H); 8.96 (broad s, 1H); 10.25 (s, 1H).<br>Mass spectrum (EI): m/z 235: [M − NHPh]$^+$ (base peak), m/z 327: [M]$^+$ |
| 48 | $^1$H NMR spectrum (d$_6$-DMSO, δ in ppm): 3.85 (s, 3H); 7.01 (dd, J = 3.0 and 8.5 Hz, 1H); 7.10 (t, J = 8.0 Hz, 1H); from 7.27 to 7.31 (m, 2H); 7.35 (broad t, J = 8.0 Hz, 2H); 7.45 (t, J = 8.5 Hz, 1H); from 7.71 to 7.78 (m, 2H); 7.91 (broad d, J = 8.0 Hz, 2H); 8.50 (s, 1H); 9.01 (broad s, 1H); 10.25 (s, 1H).<br>Mass spectrum (EI): m/z 251: [M − NHPh]$^+$ (base peak), m/z 343: [M]$^+$ |
| 49 | $^1$H NMR spectrum (d$_6$-DMSO, δ in ppm): 2.13 (very broad unresolved m, 2H); 3.81 (s, 3H); 7.10 (broad t, J = 8.0 Hz, 1H); 7.35 (broad t, J = 8.0 Hz, 2H); 7.39 (broad d, J = 7.5 Hz, 1H); 7.46 (t, J = 7.5 Hz, 1H); 7.57 (broad d, J = 7.5 Hz, 1H); 7.71 (broad s, 1H); 7.75 (d, J = 1.5 Hz, 1H); 7.91 (broad d, J = 8.0 Hz, 2H); 8.53 (s, 1H); 8.99 (broad s, 1H); 10.3 (s, 1H).<br>Mass spectrum (ES): m/z 343 [M + H]$^+$ (base peak) |
| 50 | $^1$H NMR spectrum (d$_6$-DMSO, δ in ppm): 7.10 (t, J = 8.0 Hz, 1H); 7.35 (broad t, J = 8.0 Hz, 2H); 7.51 (broad d, J = 8.0 Hz, 1H); 7.57 (t, J = 8.0 Hz, 1H); from 7.71 to 7.81 (m, 3H); 7.84 (broad s, 1H); 7.91 (broad d, J = 8.0 Hz, 2H); 8.50 (s, 1H); 9.08 (broad s, 1H); 10.3 (s, 1H).<br>Mass spectrum (ES): m/z 348 [M + H]$^+$ (base peak) |
| 51 | $^1$H NMR spectrum (d$_6$-DMSO, δ in ppm): 7.10 (t, J = 8.0 Hz, 1H); 7.35 (t, J = 8.0 Hz, 2H); 7.48 (broad m, 1H); 7.61 (t, J = 8.0 Hz, 1H); 7.80 (m, 2H); 7.91 (m, 4H); 8.12 (broad m, 1H); 8.24 (broad s, 1H); 8.54 (s, 1H); 9.08 (broad s, 1H); 10.3 (s, 1H).<br>Mass spectrum (ES): m/z 357 [M + H]$^+$ (base peak) |
| 52 | $^1$H NMR spectrum (d$_6$-DMSO, δ in ppm): 1.39 (d, J = 6.5 Hz, 3H); 4.83 (m, 1H); 5.29 (d, J = 4.0 Hz, 1H); 7.09 (t, J = 8.0 Hz, 1H); 7.36 (broad t, J = 8.0 Hz, 2H); 7.40 (broad d, J = 8.0 Hz, 1H); 7.48 (t, J = 8.0 Hz, 1H); 7.58 (broad d, J = 8.0 Hz, 1H); 7.70 (broad s, 1H); 7.76 (m, 2H); 7.90 (broad d, J = 8.0 Hz, 2H); 8.54 (s, 1H); 8.99 (broad s, 1H); 10.3 (s, 1H).<br>Mass spectrum (ES): m/z 358 [M + H$^+$] (base peak) |
| 53 | $^1$H NMR spectrum (d$_6$-DMSO, δ in ppm): 2.41 (s, 3H); 7.10 (t, J = 7.5 Hz, 1H); 7.26 (broad d, J = 8.0 Hz, 1H); 7.35 (t, J = 7.5 Hz, 2H); 7.42 (t, J = 8.0 Hz, 1H); 7.53 (broad d, J = 8.0 Hz, 1H); 7.57 (broad s, 1H); 7.74 (s, 2H); 7.91 (d, J = 7.5 Hz, 2H); 8.51 (s, 1H); 8.99 (s, 1H); 10.3 (s, 1H).<br>Mass spectrum (LC-MS-DAD-ELSD): m/z 328 [M + H]$^+$ |
| 54 | $^1$H NMR spectrum (d$_6$-DMSO, δ in ppm): 1.12 (t, J = 7.0 Hz, 6H); from 3.25 to 3.45 (masked m, 4H); 7.14 (t, J = 8.0 Hz, 1H); 7.39 (t, J = 8.0 Hz, 2H); 7.62 (broad s, 2H); 7.82 (d, J = 8.0 Hz, 2H); 8.14 (broad unresolved m, 1H); 8.61 (broad s, 1H); 10.65 (broad unresolved m, 1H).<br>Mass spectrum (LC-MS-DAD-ELSD): m/z 309 [M + H]$^+$ |
| 55 | $^1$H NMR spectrum (d$_6$-DMSO, δ in ppm): 2.83 (d, J = 6.5 Hz, 3H); 7.11 (t, J = 8.0 Hz, 1H); 7.37 (t, J = 8.0 Hz, 2H); 7.62 (t, J = 8.0 Hz, 1H); 7.80 (broad d, J = 8.0 Hz, 1H); from 7.33 to 7.95 (m, 5H); 8.20 (broad s, 1H); 8.59 (m, 2H); 9.11 (s, 1H); 10.35 (s, 1H).<br>Mass spectrum (LC-MS-DAD-ELSD): m/z 371 [M + H]$^+$, m/z 415 [M + HCO$_2$]$^-$ |
| 56 | $^1$H NMR spectrum (d$_6$-DMSO, δ in ppm): 7.10 (t, J = 7.5 Hz, 1H); 7.34 (t, J = 7.5 Hz, 2H); 7.60 (broad unresolved m, 1H); 7.69 (d, J = 9.5 Hz, 1H); 7.80 (dd, J = 1.5 and 9.5 Hz, 1H); 7.89 (d, J = 7.5 Hz, 2H); 8.14 (broad unresolved m, 1H); 8.61 (s, 1H); 9.20 (broad s, 1H); 10.3 (s, 1H). |

TABLE 2-continued

| Ex | Characterizations |
|---|---|
| 57 | $^1$H NMR spectrum (d$_6$-DMSO, δ in ppm): 2.87 (s, 6H); 6.89 (dt, J = 2.5 and 9.0 Hz, 1H); 7.35 (m, 2H); 7.51 (d, J = 10.0 Hz, 1H); 7.72 (broad dd, J = 2.5 and 9.0 Hz, 1H); 7.88 (td, J = 2.5 and 9.0 Hz, 1H); 7.90 (broad s, 1H); 8.34 (s, 1H); 13.35 (broad s, 1H).<br>Mass spectrum (LC-MS-DAD-ELSD): m/z 299 [M + H]$^+$. |
| 58 | $^1$H NMR spectrum (d$_6$-DMSO, δ in ppm): 2.88 (s, 6H); 7.00 (m, 1H); 7.39 (m, 2H); 7.55 (d, J = 9.5 Hz, 1H); 7.89 (d, J = 2.5 Hz, 1H); 8.07 (ddd, J = 3.5, 6.5 and 10.5 Hz, 1H); 8.39 (s, 1H); 9.72 (broad s, 1H).<br>Mass spectrum (LC-MS-DAD-ELSD): m/z 317 [M + H]$^+$. |
| 59 | $^1$H NMR spectrum (d$_6$-DMSO, δ in ppm): 2.87 (s, 6H); 7.22 (m, 2H); 7.38 (dd, J = 2.5 and 10.0 Hz, 1H); 7.54 (d, J = 10.0 Hz, 1H); 7.83 (m, 1H); 7.89 (d, J = 2.5 Hz, 1H); 8.38 (s, 1H); 9.89 (broad s, 1H).<br>Mass spectrum (LC-MS-DAD-ELSD): m/z 317 [M + H]$^+$. |
| 60 | $^1$H NMR spectrum (d$_6$-DMSO, δ in ppm): 2.87 (s, 6H); from 7.12 to 7.36 (m, 3H); 7.39 (dd, J = 2.5 and 10.0 Hz, 1H); 7.56 (d, J = 10.0 Hz, 1H); 7.89 (d, J = 2.5 Hz, 1H); 8.15 (dt, J = 2.5 and 8.0 Hz, 1H); 8.37 (s, 1H); 9.69 (broad s, 1H).<br>Mass spectrum (LC-MS-DAD-ELSD): m/z 299 [M + H]$^+$. |
| 61 | $^1$H NMR spectrum (d$_6$-DMSO, δ in ppm): 4.59 (broad s, 2H); 5.30 (broad s, 1H); 6.92 (dt, J = 2.5 and 9.0 Hz, 1H); 7.38 (m, 2H); 7.49 (t, J = 7.5 Hz, 1H); 7.60 (broad d, J = 7.5 Hz, 1H); 7.69 (broad s, 1H); 7.76 (m, 3H); 7.89 (td, J = 2.5 and 11.5 Hz, 1H); 8.57 (s, 1H); 9.00 (broad s, 1H); 10.55 (broad s, 1H).<br>Mass spectrum (LC-MS-DAD-ELSD): m/z 362 [M + H]$^+$. |
| 62 | $^1$H NMR spectrum (d$_6$-DMSO, δ in ppm): 4.60 (d, J = 5.5 Hz, 2H); 5.29 (t, J = 5.5 Hz, 1H); 6.93 (tt, J = 2.5 and 9.0 Hz, 1H); 7.39 (broad d, J = 7.5 Hz, 1H); 7.49 (t, J = 7.5 Hz, 1H); 7.60 (broad d, J = 7.5 Hz, 1H); 7.69 (broad s, 1H); 7.75 (m, 4H); 8.59 (s, 1H); 9.00 (t, J = 1.5 Hz, 1H); 10.8 (s, 1H).<br>Mass spectrum (LC-MS-DAD-ELSD): m/z 380 [M + H]$^+$. |
| 63 | $^1$H NMR spectrum (d$_6$-DMSO, δ in ppm): 4.60 (d, J = 5.5 Hz, 2H); 5.29 (t, J = 5.5 Hz, 1H); 7.21 (dt, J = 1.5 and 7.5 Hz, 1H); from 7.35 to 7.45 (m, 2H); 7.49 (t, J = 7.5 Hz, 1H); 7.59 (m, 2H); 7.69 (broad s, 1H); from 7.72 to 7.85 (m, 2H); 8.38 (dd, J = 1.5 and 7.5 Hz, 1H); 8.60 (s, 1H); 8.99 (broad s, 1H); 9.95 (s, 1H).<br>Mass spectrum (LC-MS-DAD-ELSD): m/z 378 [M + H]$^+$, presence of 1 Cl. |
| 64 | $^1$H NMR spectrum (d$_6$-DMSO, δ in ppm): 2.31 (s, 3H); 4.60 (d, J = 5.5 Hz, 2H); 5.29 (t, J = 5.5 Hz, 1H); 6.92 (broad d, J = 7.5 Hz, 1H); 7.22 (t, J = 7.5 Hz, 1H); 7.39 (broad d, J = 7.5 Hz, 1H); 7.49 (t, J = 7.5 Hz, 1H); 7.60 (broad d, J = 7.5 Hz, 1H); 7.68 (m, 2H); 7.73 (s, 2H); 7.76 (broad s, 1H); 8.51 (s, 1H); 8.99 (t, J = 1.5 Hz, 1H); 10.15 (s, 1H).<br>Mass spectrum (LC-MS-DAD-ELSD): m/z 358 [M + H]$^+$. |
| 65 | $^1$H NMR spectrum (d$_6$-DMSO, δ in ppm): 4.60 (d, J = 5.5 Hz, 2H); 5.29 (t, J = 5.5 Hz, 1H); 7.05 (m, 1H); 7.40 (m, 2H); 7.49 (t, J = 7.5 Hz, 1H); 7.60 (broad d, J = 7.5 Hz, 1H); 7.69 (broad s, 1H); from 7.72 to 7.84 (m, 2H); 8.02 (ddd, J = 2.5, 6.0 and 10.5 Hz, 1H); 8.59 (s, 1H); 8.99 (t, J = 1.5 Hz, 1H); 9.89 (broad s, 1H).<br>Mass spectrum (LC-MS-DAD-ELSD): m/z 380 [M + H]$^+$. |
| 66 | $^1$H NMR spectrum (d$_6$-DMSO, δ in ppm): 4.60 (d, J = 5.5 Hz, 2H); 5.29 (t, J = 5.5 Hz, 1H); 7.25 (m, 2H); 7.39 (broad d, J = 7.5 Hz, 1H); 7.49 (t, J = 7.5 Hz, 1H); 7.60 (broad d, J = 7.5 Hz, 1H); 7.69 (broad s, 1H); from 7.72 to 7.83 (m, 3H); 8.58 (s, 1H); 8.99 (broad s, 1H); 10.1 (broad s, 1H).<br>Mass spectrum (LC-MS-DAD-ELSD): m/z 380 [M + H]$^+$. |
| 67 | $^1$H NMR spectrum (d$_6$-DMSO, δ in ppm): 4.60 (d, J = 5.5 Hz, 2H); 5.29 (t, J = 5.5 Hz, 1H); from 7.18 to 7.37 (m, 3H); 7.39 (broad d, J = 7.5 Hz, 1H); 7.49 (t, J = 7.5 Hz, 1H); 7.60 (broad d, J = 7.5 Hz, 1H); 7.69 (broad s, 1H); from 7.72 to 7.82 (m, 2H); 8.10 (m, 1H); 8.57 (s, 1H); 8.99 (t, J = 1.5 Hz, 1H); 9.83 (d, J = 1.5 Hz, 1H).<br>Mass spectrum (LC-MS-DAD-ELSD): m/z 362 [M + H]$^+$. |
| 68 | $^1$H NMR spectrum (d$_6$-DMSO, δ in ppm): 4.60 (d, J = 5.5 Hz, 2H); 5.29 (t, J = 5.5 Hz, 1H); 7.28 (ddd, J = 2.0, 4.5 and 8.5 Hz, 1H); 7.40 (m, 2H); 7.49 (t, J = 7.5 Hz, 1H); 7.60 (broad d, J = 7.5 Hz, 1H); 7.69 (broad s, 1H); 7.79 (m, 2H); 8.19 (dd, J = 2.0 and 6.5 Hz, 1H); 8.59 (s, 1H); 8.99 (broad s, 1H); 9.91 (d, J = 1.5 Hz, 1H).<br>Mass spectrum (LC-MS-DAD-ELSD): m/z 396 [M + H]$^+$, presence of 1 Cl. |
| 69 | $^1$H NMR spectrum (d$_6$-DMSO, δ in ppm): 3.12 (m, 4H); 3.79 (m, 4H); 7.12 (t, J = 8.0 Hz, 1H); 7.38 (t, J = 8.0 Hz, 2H); from 7.60 to 7.74 (m, 2H); 7.83 (d, J = 8.0 Hz, 2H); 8.25 (s, 1H); 8.59 (s, 1H); 10.5 (broad unresolved m, 1H).<br>Mass spectrum (LC-MS-DAD-ELSD): m/z 323 [M + H]$^+$. |
| 70 | $^1$H NMR spectrum (d$_6$-DMSO, δ in ppm): 2.32 (m, 2H); 3.82 (t, J = 7.5 Hz, 4H); 6.91 (dd, J = 1.5 and 9.5 Hz, 1H); 7.08 (t, J = 7.5 Hz, 1H); 7.32 (t, J = 7.5 Hz, 2H); 7.52 (d, J = 9.5 Hz, 1H); 7.70 (d, J = 1.5 Hz, 1H); 7.89 (d, J = 7.5 Hz, 2H); 8.31 (s, 1H); 10.15 (s, 1H).<br>Mass spectrum (LC-MS-DAD-ELSD): m/z 293 [M + H]$^+$. |
| 71 | $^1$H NMR spectrum (d$_6$-DMSO, δ in ppm): 2.89 (s, 3H); 7.10 (tt, J = 1.5 and 7.5 Hz, 1H); 7.33 (t, J = 7.5 Hz, 2H); 7.39 (d, J = 9.5 Hz, 1H); 7.70 (d, J = 9.5 Hz, 1H); 7.90 (d, J = 7.5 Hz, 2H); 8.49 (s, 1H); 10.3 (s, 1H).<br>Mass spectrum (LC-MS-DAD-ELSD): m/z 378 [M + H]$^+$. |

TABLE 2-continued

| Ex | Characterizations |
|---|---|
| 72 | ¹H NMR spectrum (d₆-DMSO, δ in ppm): 6.92 (tt, J = 2.0 and 9.0 Hz, 1H); 7.51 (d, J = 9.5 Hz, 1H); 7.59 (dd, J = 1.5 and 9.5 Hz, 1H); 7.72 (m, 2H); 8.47 (s, 1H); 9.02 (broad s, 1H); 10.75 (s, 1H).<br>Mass spectrum (LC-MS-DAD-ELSD): m/z 398 [M − H]⁻; m/z 400 [M + H]⁺. |
| 73 | ¹H NMR spectrum (d₆-DMSO, δ in ppm): 4.61 (s, 2H); 7.15 (dm, J = 8.0 Hz, 1H); 7.38 (m, 2H); 7.49 (t, J = 8.0 Hz, 1H); 7.61 (broad d, J = 8.0 Hz, 1H); 7.69 (broad s, 1H); 7.77 (m, 2H); 7.87 (dm, J = 8.0 Hz, 1H); 8.12 (t, J = 2.0 Hz, 1H); 8.58 (s, 1H); 9.01 (broad s, 1H); 10.55 (s, 1H).<br>Mass spectrum (UPLC-MS-DAD-ELSD): m/z 376 [M − H]⁻; m/z 378 [M + H]⁺, presence of 1 Cl. |
| 74 | ¹H NMR spectrum (d₆-DMSO, δ in ppm): 2.87 (s, 6H); 6.90 (tt, J = 2.5 and 9.5 Hz, 1H); 7.35 (dd, J = 2.5 and 10.0 Hz, 1H); 7.51 (d, J = 10.0 Hz, 1H); 7.72 (m, 2H); 7.89 (d, J = 2.5 Hz, 1H); 8.37 (s, 1H); 10.6 (broad s, 1H).<br>Mass spectrum (UPLC-MS-DAD-ELSD): m/z 317 [M + H]⁺. |
| 75 | ¹H NMR spectrum (d₆-DMSO, δ in ppm): 2.88 (s, 6H); 7.18 (dt, J = 1.5 and 7.5 Hz, 1H); from 7.32 to 7.43 (m, 2H); 7.57 (m, 2H); 7.89 (d, J = 2.5 Hz, 1H); 8.38 (s, 1H); 8.40 (dd, J = 1.5 and 7.5 Hz, 1H); 9.86 (s, 1H).<br>Mass spectrum (UPLC-MS-DAD-ELSD): m/z 315 [M + H]⁺, presence of 1 Cl. |
| 76 | ¹H NMR spectrum (d₆-DMSO, δ in ppm): 2.87 (s, 6H); 7.04 (dm, J = 8.0 Hz, 1H); 7.37 (dd, J = 2.5 and 10.0 Hz, 1H); 7.44 (t, J = 8.0 Hz, 1H); 7.51 (d, J = 10.0 Hz, 1H); 7.89 (m, 2H); 8.09 (broad s, 1H); 8.36 (s, 1H); 10.5 (s, 1H).<br>Mass spectrum (UPLC-MS-DAD-ELSD): m/z 365 [M + H]⁺. |
| 77 | ¹H NMR spectrum (d₆-DMSO, δ in ppm): 4.61 (d, J = 6.0 Hz, 2H); 5.29 (t, J = 6.0 Hz, 1H); 7.27 (dt; J = 1.5 and 8.0 Hz, 1H); from 7.35 to 7.44 (m, 2H); 7.49 (t, J = 8.0 Hz, 1H); 7.61 (broad d, J = 8.0 Hz, 1H); 7.69 (broad s, 1H); 7.78 (m, 2H); 7.94 (dt, J = 1.5 and 8.0 Hz, 1H); 8.58 (s, 1H); 8.99 (broad s, 1H); 10.05 (s, 1H).<br>Mass spectrum (UPLC-MS-DAD-ELSD): m/z 394 [M − H]⁻; m/z 396 [M + H]⁺, presence of 1 Cl. |
| 78 | ¹H NMR spectrum (d₆-DMSO, δ in ppm): 2.30 (s, 3H); 2.87 (s, 6H); 6.89 (broad d, J = 7.5 Hz, 1H); 7.21 (t, J = 7.5 Hz, 1H); 7.33 (dd, J = 2.5 and 10.0 Hz, 1H); 7.50 (d, J = 10.0 Hz, 1H); 7.63 (broad d, J = 7.5 Hz, 1H); 7.71 (broad s, 1H); 7.89 (d, J = 2.5 Hz, 1H); 8.31 (s, 1H); 9.94 (s, 1H).<br>Mass spectrum (UPLC-MS-DAD-ELSD): m/z 295 [M + H]⁺ |
| 79 | ¹H NMR spectrum (d₆-DMSO, δ in ppm): 2.87 (s, 6H); 7.12 (ddd, J = 1.0, 2.0 and 8.0 Hz, 1H); 7.35 (m, 2H); 7.51 (d, J = 10.0 Hz, 1H); 7.83 (ddd, J = 1.0, 2.0 and 8.0 Hz, 1H); 7.89 (d, J = 2.5 Hz, 1H); 8.11 (t, J = 2.0 Hz, 1H); 8.35 (s, 1H); 10.35 (s, 1H).<br>Mass spectrum (UPLC-MS-DAD-ELSD): m/z 315 [M + H]⁺, presence of 1 Cl. |
| 80 | ¹H NMR spectrum (d₆-DMSO, δ in ppm): 2.88 (s, 6H); 7.24 (ddd, J = 2.5, 4.5 and 9.0 Hz, 1H); 7.29 (m, 2H); 7.54 (d, J = 10.0 Hz, 1H); 7.89 (d, J = 2.5 Hz, 1H); 8.23 (dd, J = 2.5 and 6.5 Hz, 1H); 8.39 (s, 1H); 9.75 (d, J = 2.0 Hz, 1H).<br>Mass spectrum (UPLC-MS-DAD-ELSD): m/z 333 [M + H]⁺, presence of 1 Cl. |
| 81 | ¹H NMR spectrum (d₆-DMSO, δ in ppm): 2.88 (s, 6H); 7.25 (dt, J = 1.5 and 8.0 Hz, 1H); 7.38 (m, 2H); 7.54 (d, J = 10.0 Hz, 1H); 7.89 (d, J = 2.5 Hz, 1H); 8.00 (dt, J = 1.5 and 8.0 Hz, 1H); 8.38 (s, 1H); 9.88 (broad s, 1H).<br>Mass spectrum (UPLC-MS-DAD-ELSD): m/z 333 [M + H]⁺, presence of 1 Cl. |
| 82 | ¹H NMR spectrum (d₆-DMSO, δ in ppm): 2.87 (s, 6H); 6.88 (dd, J = 2.5 and 8.0 Hz, 1H); 7.21 (t, J = 74.0 Hz, 1H); 7.38 (m, 2H); 7.51 (d, J = 10.0 Hz, 1H); 7.74 (dm, J = 8.0 Hz, 1H); 7.89 (m, 2H); 8.34 (s, 1H); 10.3 (s, 1H).<br>Mass spectrum (UPLC-MS-DAD-ELSD): m/z 347 [M + H]⁺. |
| 83 | ¹H NMR spectrum (d₆-DMSO, δ in ppm): 2.88 (s, 6H); 7.36 (dd, J = 2.5 and 10.0 Hz, 1H); 7.41 (broad d, J = 8.0 Hz, 1H); 7.52 (d, J = 10.0 Hz, 1H); 7.58 (t, J = 8.0 Hz, 1H); 7.90 (d, J = 2.5 Hz, 1H); 8.13 (broad d, J = 8.0 Hz, 1H); 8.38 (s, 1H); 8.42 (broad s, 1H); 10.55 (s, 1H).<br>Mass spectrum (UPLC-MS-DAD-ELSD): m/z 349 [M + H]⁺. |

The compounds according to the invention have formed the subject of pharmacological assays which make it possible to determine their modulatory effects on NOT.

Evaluation of the In Vitro Activity on N2A Cells

On a cell line (N2A) endogenously expressing the mouse Nurr1 receptor and stably transfected with the NOT binding response element (NBRE) coupled to the luciferase reporter gene. The $EC_{50}$ values are between 0.01 and 1000 nM. The assays were carried out according to the procedure described below.

The Neuro-2A cell line comes from a standard commercial source (ATCC). The Neuro-2A clone was obtained, from a spontaneous tumor originating from an A albino mouse strain, by R. J Klebe et al. This Neuro-2A line is subsequently stably transfected with 8NBRE-luciferase. The N2A-8NBRE cells are cultured until confluence in 75 cm² culture flasks containing DMEM supplemented with 10% of fetal calf serum, 4.5 g/l of glucose and 0.4 mg/ml of geneticin. After a week of culture, the cells are recovered with 0.25% trypsin for 30 seconds and then resuspended in DMEM without phenol red, containing 4.5 g/l of glucose and 10% of Hyclone delipidized serum, and deposited into transparent-bottom 96-well white plates. The cells are deposited at a rate of 60 000 per well in 75 μl for 24 hours before the addition of the products. The products are applied in 25 μl and incubated for a further 24 hours. On the day of the measurement, an equivalent volume (100 μl) of Steadylite is added to each well and then left for a period of 30 minutes in order to obtain complete cell lysis and maximum signal production. The plates are subsequently measured in a luminescence counter for microplates after having been sealed with an adhesive film. The products are prepared in the form of a stock solution at $10^{-2}$M and then diluted in 100% of DMSO. Each product concentration is prediluted in culture medium before incubation with the cells, thus containing 0.625% final concentration of DMSO.

For example, compounds Nos. 4, 7, 19, 29, 32, 43, 58, 67 and 70 showed an $EC_{so}$ value of 0.66 nM, 0.9 nM, 0.6 nM, 1.3 nM, 0.06 nM, 0.3 nM, 1.3 nM, 0.7 nM and 0.16 nM respectively.

Evaluation of the Binding to the Human NOT Receptor

The direct binding between compounds of the invention and the human NOT receptor was evaluated using SPR (surface plasmon resonance) technology. In this assay, the protein is immobilized covalently at the matrix and the molecule to be studied is injected into the chamber comprising the sensor chip. The signal is directly proportional to the amount of product bound to the protein. The binding assays were carried out in a Biacore S51 instrument (Biacore Inc., Piscataway, N.J.). The GST-NOT (NOT-FL) whole protein was provided by Invitrogen (PV3265). The NOT ligand-binding domain (His-Thr-NOT 329-598) was expressed and purified as described in *Nature*, 423, 555-560. The two proteins, diluted to a concentration of 20 μg/ml in an acetate buffer, pH 5.0, containing 5 mM of DTT, were immobilized on a carboxymethyl 5' dextran surface (CM5 sensor chip, Biacore Inc.) by amine coupling according to the protocol recommended by Biacore, elution being carried out with an HBS-N buffer (10 mM HEPES, 0.15 M NaCl, 3 mM EDTA, pH 7.4). Approximately 10 000-15 000 resonance units (RU) of the proteins are captured on the surface of the CM5 sensor chip. The stock solutions of the compounds to be studied, at 1.5 mM in DMSO, are serially diluted in elution buffer (50 mM HEPES pH 8; 150 mM NaCl; 10 mM $MgCl_2$; 2% DMSO, 1 mM DTT) to concentrations ranging from 3.75 to 0.1 μM. Each product concentration is injected at 4° C. for 1 minute at 30 μl/min. The dissociation was recorded for 5 minutes without any other procedure for regenerating the surface. The signals obtained are corrected by testing each product concentration on an unmodified dextran surface (blank). The signal due to the migration buffer is deducted from the total signal ("double referencing"), as is the effect of the DMSO. The signal analysis is carried out using the Biacore S51 analytical software (version 1.2.1). The compounds are subsequently classified according to their maximum binding level and according to kinetic parameters for binding to the immobilized protein.

By way of example, compounds Nos. 19 and 7 have a respectively low and moderate affinity.

It is thus apparent that the compounds according to the invention have a modulatory effect on NOT.

The compounds according to the invention can thus be used in the preparation of medicaments for their therapeutic application in the treatment or prevention of diseases involving NOT receptors.

Thus, according to another of its aspects, a subject matter of the invention is medicaments which comprise a compound of formula (I) or an addition salt of the latter with a pharmaceutically acceptable acid.

These medicaments are employed therapeutically, in particular in the treatment and prevention of neurodegenerative diseases, such as, for example, Parkinson's disease, Alzheimer's disease, tauopathies (for example, progressive supranuclear palsy) or multiple sclerosis; cerebral traumas, such as ischemia and cranial traumas and epilepsy; psychiatric diseases, such as schizophrenia, depression, substance dependence or attention deficit hyperactivity disorders; inflammatory diseases, such as vascular pathologies, atherosclerosis, inflammations of the joints, arthrosis, rheumatoid arthritis, osteoarthritis or allergic inflammatory diseases, such as asthma; and to complete the treatment of osteoporosis; or cancers.

These compounds might also be used as treatment associated with stem cell transplants and/or grafts.

According to another of its aspects, the present invention relates to pharmaceutical compositions comprising, as active principle, a compound according to the invention. These pharmaceutical compositions comprise an effective dose of at least one compound according to the invention or a pharmaceutically acceptable salt of said compound, and also at least one pharmaceutically acceptable excipient.

Said excipients are chosen, depending on the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its salt can be administered in unit administration form, as a mixture with conventional pharmaceutical excipients, to animals and human beings for the prophylaxis or treatment of the above disorders or diseases.

The appropriate unit administration forms comprise oral forms, such as tablets, soft or hard gelatin capsules, powders, granules and oral solutions or suspensions, forms for sublingual, buccal, intratracheal, intraocular or intranasal administration or for administration by inhalation, forms for topical, transdermal, subcutaneous, intramuscular or intravenous administration, forms for rectal administration and implants. For topical application, the compounds according to the invention can be used in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

There may be specific cases where higher or lower dosages are appropriate; such dosages do not depart from the scope of the invention. According to the usual practice, the dosage appropriate to each patient is determined by the physician according to the method of administration and the weight and the response of said patient.

The present invention, according to another of its aspects, also relates to a method for the treatment of the pathologies indicated above which comprises the administration, to a patient, of an effective dose of a compound according to the invention or one of its pharmaceutically acceptable salts.

We claim:
1. A method for treating multiple sclerosis, cerebral trauma, epilepsy, osteoporosis, Parkinson's disease, Alzheimer's disease, tauopathy, schizophrenia, depression, or substance dependence in a patient in need thereof, comprising administering to the patient a pharmaceutically effective amount of a compound of formula (I):

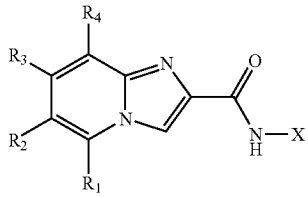

wherein:
X is phenyl optionally substituted by one or more groups chosen, independently of one another, from the group consisting of halogen, $(C_1-C_6)$alkoxy, $(C_1-C_6)$alkyl, $(C_3-C_7)$cycloalkyl$(C_1-C_6)$alkyl, $(C_3-C_7)$cycloalkyl$(C_1-C_6)$alkoxy, and NRaRb;
$R_1$ is hydrogen, halogen, $(C_1-C_6)$alkoxy, $(C_1-C_6)$alkyl, $(C_3-C_7)$cycloalkyl$(C_1-C_6)$alkyl, $(C_3-C_7)$cycloalkyl$(C_1-C_6)$alkoxy, amino or NRcRd, wherein the alkyl and alkoxy groups are optionally substituted by one or more halogen, hydroxyl, amino, or $(C_1-C_6)$alkoxy;
$R_2$ is hydrogen,
  $(C_1-C_6)$alkyl optionally substituted by one or more groups chosen, independently of one another, from the group consisting of hydroxyl, halogen, amino, NRaRb and phenyl,
  $(C_1-C_6)$alkoxy optionally substituted by one or more groups chosen, independently of one another, from the group consisting of hydroxyl, halogen, amino, and NRaRb,
  $(C_3-C_7)$cycloalkyl$(C_1-C_6)$alkyl,
  $(C_3-C_7)$cycloalkyl$(C_1-C_6)$alkoxy,
  $(C_2-C_6)$alkenyl,
  $(C_2-C_6)$alkynyl,
  —CO—$R_5$,
  —CO—$NR_6R_7$,
  —CO—O—$R_8$,
  —$NR_9$—CO—$R_{10}$,
  —$NR_{11}R_{12}$,
  halogen,
  cyano, or
  phenyl optionally substituted by one or more groups chosen, independently of one another, from the group consisting of halogen, $(C_1-C_6)$alkoxy, NRaRb, —CO—$R_5$, —CO—$NR_6R_7$, —CO—O—$R_8$, $(C_3-C_7)$cycloalkyl$(C_1-C_6)$alkyl, $(C_3-C_7)$cycloalkyl-$(C_1-C_6)$alkoxy, and $(C_1-C_6)$alkyl optionally substituted by one or more hydroxyl or NRaRb;
$R_3$ is hydrogen, $(C_1-C_6)$alkyl, $(C_1-C_6)$alkoxy or halogen;
$R_4$ is hydrogen, $(C_1-C_4)$alkyl, $(C_1-C_4)$alkoxy or fluorine;
$R_5$ is hydrogen, phenyl or $(C_1-C_6)$alkyl;
$R_6$ and $R_7$ are independently hydrogen or $(C_1-C_6)$alkyl, or
$R_6$ and $R_7$, taken together with the nitrogen atom to which they are attached, form a 4- to 7-membered ring optionally including another heteroatom chosen from the group consisting of N, O and S;
$R_8$ is $(C_1-C_6)$alkyl;
$R_9$ and $R_{10}$ are independently hydrogen or $(C_1-C_6)$alkyl;
$R_{11}$ and $R_{12}$ are independently $(C_1-C_6)$alkyl, or
$R_{11}$ and $R_{12}$, taken together with the nitrogen atom to which they are attached, form a 4- to 7-membered ring optionally including another heteroatom chosen from the group consisting of N, O and S;
Ra and Rb are independently hydrogen or $(C_1-C_6)$alkyl, or
Ra and Rb, taken together with the nitrogen atom to which they are attached, form a 4- to 7-membered ring;
Rc is hydrogen; and
Rd is $(C_1-C_6)$alkyl;
provided that:
at least one of $R_1$, $R_2$, $R_3$ and $R_4$ is other than hydrogen,
when $R_3$ is methyl, then X is unsubstituted,
when $R_1$ is methyl, then X is unsubstituted, and
when $R_2$ is chlorine, then X is not a para-fluorophenyl;
or a pharmaceutically acceptable salt thereof.

2. The method according to claim 1, wherein X is phenyl.
3. The method according to claim 1, wherein $R_1$, $R_3$ and $R_4$ are hydrogen.
4. The method according to claim 1, wherein the compound of formula (I) is:
  6-Chloro-N-phenylimidazo[1,2-a]pyridine-2-carboxamide,
  8-Methyl-N-phenylimidazo[1,2-c]pyridine-2-carboxamide,
  6-(Dimethylamino)-N-phenylimidazo[1,2-c]pyridine-2-carboxamide,
  6-(1-Hydroxy-1-methylethyl)-N-phenylimidazo[1,2-a]pyridine-2-carboxamide,
  N-(4-Fluorophenyl)-6-isopropenylimidazo[1,2-a]pyridine-2-carboxamide,
  6-Chloro-N-(2-chlorophenyl)imidazo[1,2-a]pyridine-2-carboxamide,
  N,6-Diphenylimidazo[1,2-c]pyridine-2-carboxamide,
  N-Phenyl-6-vinylimidazo[1,2-a]pyridine-2-carboxamide,
  6-Ethyl-N-phenylimidazo[1,2-c]pyridine-2-carboxamide,
  6-Formyl-N-phenylimidazo[1,2-a]pyridine-2-carboxamide,
  6-Ethynyl-N-phenylimidazo[1,2-c]pyridine-2-carboxamide,
  6-[3-(1-Hydroxy-1-methylethyl)phenyl]-N-phenylimidazo[1,2-c]pyridine-2-carboxamide,
  6-[Hydroxy(phenyl)methyl]-N-phenylimidazo[1,2-a]pyridine-2-carboxamide,
  6-Acetyl-N-phenylimidazo[1,2-c]pyridine-2-carboxamide hydrochloride (1:1),
  6-Isopropyl-N-phenylimidazo[1,2-a]pyridine-2-carboxamide,
  6-(1-Hydroxyethyl)-N-phenylimidazo[1,2-a]pyridine-2-carboxamide,
  6-Acetamido-N-phenylimidazo[1,2-a]pyridine-2-carboxamide,
  6-(Dimethylamino)-5-methyl-N-phenylimidazo[1,2-c]pyridine-2-carboxamide,
  6-Methyl-N-phenylimidazo[1,2-c]pyridine-2-carboxamide,
  5-Methyl-N-phenylimidazo[1,2-c]pyridine-2-carboxamide,
  7-Methyl-N-phenylimidazo[1,2-c]pyridine-2-carboxamide,
  6-Bromo-N-phenylimidazo[1,2-c]pyridine-2-carboxamide,
  6-Fluoro-N-phenylimidazo[1,2-c]pyridine-2-carboxamide,
  6,8-Difluoro-N-phenylimidazo[1,2-c]pyridine-2-carboxamide,
  6-Bromo-5-methyl-N-phenylimidazo[1,2-c]pyridine-2-carboxamide,
  6-Iodo-N-phenylimidazo[1,2-c]pyridine-2-carboxamide, 6-Cyano-N-phenylimidazo[1,2-c]pyridine-2-carboxamide,
6-(Hydroxymethyl)-N-phenylimidazo[1,2-c]pyridine-2-carboxamide,
6-Methoxy-N-phenylimidazo[1,2-c]pyridine-2-carboxamide,
N-(4-fluorophenyl)-6-(1-hydroxy-1-methylethyl)imidazo[1,2-c]pyridine-2-carboxamide,
6-Benzoyl-N-phenylimidazo[1,2-c]pyridine-2-carboxamide,
6-Isopropenyl-N-phenylimidazo[1,2-c]pyridine-2-carboxamide,
6-Chloro-N-(3-fluorophenyl)imidazo[1,2-c]pyridine-2-carboxamide,
6-Chloro-N-(3-chlorophenyl)imidazo[1,2-c]pyridine-2-carboxamide,
6-Chloro-N-(3-methoxyphenyl)imidazo[1,2-c]pyridine-2-carboxamide,
6-Chloro-N[4-(dimethylamino)phenyl]imidazo[1,2-c]pyridine-2-carboxamide,
6-Chloro-N-(4-chlorophenyl)imidazo[1,2-c]pyridine-2-carboxamide,
6-[2-(Hydroxymethyl)phenyl]-N-phenylimidazo[1,2-c]pyridine-2-carboxamide,
6-[3-(Hydroxymethyl)phenyl]-N-phenylimidazo[1,2-c]pyridine-2-carboxamide,
6-[4-(Hydroxymethyl)phenyl]-N-phenylimidazo[1,2-c]pyridine-2-carboxamide,
6-(2-Formylphenyl)-N-phenylimidazo[1,2-c]pyridine-2-carboxamide,
6-(3-Formylphenyl)-N-phenylimidazo[1,2-c]pyridine-2-carboxamide,
5,6-Dimethyl-N-phenylimidazo[1,2-c]pyridine-2-carboxamide,
Methyl 3-[2-(anilinocarbonyl)imidazo[1,2-c]pyridin-6-yl]benzoate,
6-(3-Acetylphenyl)-N-phenylimidazo[1,2-c]pyridine-2-carboxamide,
6-(3-Fluorophenyl)-N-phenylimidazo[1,2-c]pyridine-2-carboxamide,
6-(4-Methylphenyl)-N-phenylimidazo[1,2-c]pyridine-2-carboxamide,
6-(3-Methoxyphenyl)-N-phenylimidazo[1,2-a]pyridine-2-carboxamide,
6-[3-(Aminomethyl)phenyl]-N-phenylimidazo[1,2-a]pyridine-2-carboxamide,
6-(3-Chlorophenyl)-N-phenylimidazo[1,2-a]pyridine-2-carboxamide,
6-(3-Carbamoylphenyl)-N-phenylimidazo[1,2-a]pyridine-2-carboxamide,
6-[3-(1-Hydroxyethyl)phenyl]-N-phenylimidazo[1,2-a]pyridine-2-carboxamide,
6-(3-Methylphenyl)-N-phenylimidazo[1,2-a]pyridine-2-carboxamide,
6-(Diethylamino)-N-phenylimidazo[1,2-a]pyridine-2-carboxamide or its hydrochloride (1:1),
6-[3-(Methylcarbamoyl)phenyl]-N-phenylimidazo[1,2-a]pyridine-2-carboxamide or its hydrochloride (1:1),
6-Carbamoyl-N-phenylimidazo[1,2-a]pyridine-2-carboxamide,
6-(Dimethylamino)-N-(3-fluorophenyl)imidazo[1,2-a]pyridine-2-carboxamide,
N-(2,5-Difluorophenyl)-6-(dimethylamino)imidazo[1,2-a]pyridine-2-carboxamide,
N-(2,3-Difluorophenyl)-6-(dimethylamino)imidazo[1,2-a]pyridine-2-carboxamide,
6-(Dimethylamino)-N-(2-fluorophenyl)imidazo[1,2-a]pyridine-2-carboxamide,
N-(3-Fluorophenyl)-6-[3-(hydroxymethyl)phenyl]imidazo[1,2-a]pyridine-2-carboxamide,
N-(3,5-Difluorophenyl)-6-[3-(hydroxymethyl)phenyl]imidazo[1,2-a]pyridine-2-carboxamide,
N-(2-Chlorophenyl)-6-[3-(hydroxymethyl)phenyl]imidazo[1,2-a]pyridine-2-carboxamide,
6-[3-(Hydroxymethyl)phenyl]-N-(3-methylphenyl)imidazo[1,2-a]pyridine-2-carboxamide,
N-(2,5-Difluorophenyl)-6-[3-(hydroxymethyl)phenyl]imidazo[1,2-a]pyridine-2-carboxamide,
N-(2,3-Difluorophenyl)-6-[3-(hydroxymethyl)phenyl]imidazo[1,2-a]pyridine-2-carboxamide,
N-(2-Fluorophenyl)-6-[3-(hydroxymethyl)phenyl]imidazo[1,2-a]pyridine-2-carboxamide,
N-(5-Chloro-2-fluorophenyl)-6-[3-(hydroxymethyl)phenyl]imidazo[1,2-a]pyridine-2-carboxamide,
6-Morpholin-4-yl-N-phenylimidazo[1,2-c]pyridine-2-carboxamide or its hydrochloride (1:1),
6-Azetidin-1-yl-N-phenylimidazo[1,2-c]pyridine-2-carboxamide,
6-Iodo-5-methyl-N-phenylimidazo[1,2-c]pyridine-2-carboxamide,
N-(3,5-Difluorophenyl)-6-iodoimidazo[1,2-c]pyridine-2-carboxamide,
N-(3-Chlorophenyl)-6-[3-(hydroxymethyl)phenyl]imidazo[1,2-c]pyridine-2-carboxamide,
N-(3,5-Difluorophenyl)-6-(dimethylamino)imidazo[1,2-c]pyridine-2-carboxamide,
N-(2-Chlorophenyl)-6-(dimethylamino)imidazo[1,2-c]pyridine-2-carboxamide,
6-(Dimethylamino)-N[3-(trifluoromethoxy)phenyl]imidazo[1,2-c]pyridine-2-carboxamide,
N-(3-Chloro-2-fluorophenyl)-6-[3-(hydroxymethyl)phenyl]imidazo[1,2-a]pyridine-2-carboxamide,
6-(Dimethylamino)-N-(3-methylphenyl)imidazo[1,2-c]pyridine-2-carboxamide,
N-(3-Chlorophenyl)-6-(dimethylamino)imidazo[1,2-c]pyridine-2-carboxamide,
N-(5-Chloro-2-fluorophenyl)-6-(dimethylamino)imidazo[1,2-c]pyridine-2-carboxamide,
N-(3-Chloro-2-fluorophenyl)-6-(dimethylamino)imidazo[1,2-c]pyridine-2-carboxamide,
N-[3-(Difluoromethoxy)phenyl]-6-(dimethylamino)imidazo[1,2-c]pyridine-2-carboxamide, or
6-(Dimethylamino)-N-[3-(trifluoromethyl)phenyl]imidazo[1,2-c]pyridine-2-carboxamide.

5. A method for treating Parkinson's disease in a patient in need thereof, comprising administering to the patient a pharmaceutically effective amount of a compound for treating Parkinson's disease of formula (I):

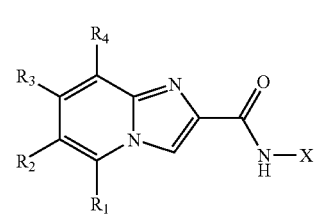

wherein:
X is phenyl optionally substituted by one or more groups chosen, independently of one another, from the group consisting of halogen, $(C_1$-$C_6)$alkoxy, $(C_1$-$C_6)$alkyl, $(C_3$-$C_7)$cycloalkyl$(C_1$-$C_6)$alkyl, $(C_3$-$C_7)$cycloalkyl$(C_1$-$C_6)$alkoxy, and NRaRb;

$R_1$ is hydrogen, halogen, $(C_1$-$C_6)$alkoxy, $(C_1$-$C_6)$alkyl, $(C_3$-$C_7)$cycloalkyl$(C_1$-$C_6)$alkyl, $(C_3$-$C_7)$cycloalkyl$(C_1$-$C_6)$alkoxy, amino or NRcRd, wherein the alkyl and alkoxy groups are optionally substituted by one or more halogen, hydroxyl, amino, or $(C_1$-$C_6)$alkoxy;

$R_2$ is hydrogen,
- $(C_1$-$C_6)$alkyl optionally substituted by one or more groups chosen, independently of one another, from the group consisting of hydroxyl, halogen, amino, NRaRb and phenyl,
- $(C_1$-$C_6)$alkoxy optionally substituted by one or more groups chosen, independently of one another, from the group consisting of hydroxyl, halogen, amino, and NRaRb,
- $(C_3$-$C_7)$cycloalkyl$(C_1$-$C_6)$alkyl,
- $(C_3$-$C_7)$cycloalkyl$(C_1$-$C_6)$alkoxy,
- $(C_2$-$C_6)$alkenyl,
- $(C_2$-$C_6)$alkynyl,
- —CO—$R_5$,
- —CO—$NR_6R_7$,
- —CO—O—$R_8$,
- —$NR_9$—CO—$R_{10}$,
- —$NR_{11}R_{12}$,
- halogen,
- cyano, or
- phenyl optionally substituted by one or more groups chosen, independently of one another, from the group consisting of halogen, $(C_1$-$C_6)$alkoxy, NRaRb, —CO—$R_5$, —CO—$NR_6R_7$, —CO—O—$R_8$, $(C_3$-$C_7)$cycloalkyl$(C_1$-$C_6)$alkyl, $(C_3$-$C_7)$cycloalkyl-$(C_1$-$C_6)$alkoxy, and $(C_1$-$C_6)$alkyl optionally substituted by one or more hydroxyl or NRaRb;

$R_3$ is hydrogen, $(C_1$-$C_6)$alkyl, $(C_1$-$C_6)$alkoxy or halogen;
$R_4$ is hydrogen, $(C_1$-$C_4)$alkyl, $(C_1$-$C_4)$alkoxy or fluorine;
$R_5$ is hydrogen, phenyl or $(C_1$-$C_6)$alkyl;
$R_6$ and $R_7$ are independently hydrogen or $(C_1$-$C_6)$alkyl, or
$R_6$ and $R_7$, taken together with the nitrogen atom to which they are attached, form a 4- to 7-membered ring optionally including another heteroatom chosen from the group consisting of N, O and S;
$R_8$ is $(C_1$-$C_6)$alkyl;
$R_9$ and $R_{10}$ are independently hydrogen or $(C_1$-$C_6)$alkyl;
$R_{11}$ and $R_{12}$ are independently $(C_1$-$C_6)$alkyl, or
$R_{11}$ and $R_{12}$, taken together with the nitrogen atom to which they are attached, form a 4- to 7-membered ring optionally including another heteroatom chosen from the group consisting of N, O and S;
Ra and Rb are independently hydrogen or $(C_1$-$C_6)$alkyl, or
Ra and Rb, taken together with the nitrogen atom to which they are attached, form a 4- to 7-membered ring;
Rc is hydrogen; and
Rd is $(C_1$-$C_6)$alkyl;
provided that:
at least one of $R_1$, $R_2$, $R_3$ and $R_4$ is other than hydrogen, when $R_3$ is methyl, then X is unsubstituted, when $R_1$ is methyl, then X is unsubstituted, and when $R_2$ is chlorine, then X is not a para-fluorophenyl;
or a pharmaceutically acceptable salt thereof.

6. The method according to claim 5, wherein X is phenyl.

7. The method according to claim 5, wherein $R_1$, $R_3$ and $R_4$ are hydrogen.

8. The method according to claim 5, wherein the compound of formula (I) is:
- 6-Chloro-N-phenylimidazo[1,2-c]pyridine-2-carboxamide,
- 8-Methyl-N-phenylimidazo[1,2-c]pyridine-2-carboxamide,
- 6-(Dimethylamino)-N-phenylimidazo[1,2-c]pyridine-2-carboxamide,
- 6-(1-Hydroxy-1-methylethyl)-N-phenylimidazo[1,2-c]pyridine-2-carboxamide,
- N-(4-Fluorophenyl)-6-isopropenylimidazo[1,2-c]pyridine-2-carboxamide,
- 6-Chloro-N-(2-chlorophenyl)imidazo[1,2-c]pyridine-2-carboxamide,
- N,6-Diphenylimidazo[1,2-c]pyridine-2-carboxamide,
- N-Phenyl-6-vinylimidazo[1,2-c]pyridine-2-carboxamide,
- 6-Ethyl-N-phenylimidazo[1,2-c]pyridine-2-carboxamide,
- 6-Formyl-N-phenylimidazo[1,2-c]pyridine-2-carboxamide,
- 6-Ethynyl-N-phenylimidazo[1,2-c]pyridine-2-carboxamide,
- 6-[3-(1-Hydroxy-1-methylethyl)phenyl]-N-phenylimidazo[1,2-c]pyridine-2-carboxamide,
- 6-[Hydroxy(phenyl)methyl]-N-phenylimidazo[1,2-c]pyridine-2-carboxamide,
- 6-Acetyl-N-phenylimidazo[1,2-c]pyridine-2-carboxamide hydrochloride (1:1),
- 6-Isopropyl-N-phenylimidazo[1,2-c]pyridine-2-carboxamide,
- 6-(1-Hydroxyethyl)-N-phenylimidazo[1,2-c]pyridine-2-carboxamide,
- 6-Acetamido-N-phenylimidazo[1,2-c]pyridine-2-carboxamide,
- 6-(Dimethylamino)-5-methyl-N-phenylimidazo[1,2-c]pyridine-2-carboxamide,
- 6-Methyl-N-phenylimidazo[1,2-c]pyridine-2-carboxamide,
- 5-Methyl-N-phenylimidazo[1,2-c]pyridine-2-carboxamide,
- 7-Methyl-N-phenylimidazo[1,2-c]pyridine-2-carboxamide,
- 6-Bromo-N-phenylimidazo[1,2-c]pyridine-2-carboxamide,
- 6-Fluoro-N-phenylimidazo[1,2-c]pyridine-2-carboxamide,
- 6,8-Difluoro-N-phenylimidazo[1,2-c]pyridine-2-carboxamide,
- 6-Bromo-5-methyl-N-phenylimidazo[1,2-c]pyridine-2-carboxamide,
- 6-Iodo-N-phenylimidazo[1,2-c]pyridine-2-carboxamide,
- 6-Cyano-N-phenylimidazo[1,2-c]pyridine-2-carboxamide,
- 6-(Hydroxymethyl)-N-phenylimidazo[1,2-c]pyridine-2-carboxamide,
- 6-Methoxy-N-phenylimidazo[1,2-c]pyridine-2-carboxamide,
- N-(4-fluorophenyl)-6-(1-hydroxy-1-methylethyl)imidazo[1,2-c]pyridine-2-carboxamide,
- 6-Benzoyl-N-phenylimidazo[1,2-c]pyridine-2-carboxamide,
- 6-Isopropenyl-N-phenylimidazo[1,2-c]pyridine-2-carboxamide,
- 6-Chloro-N-(3-fluorophenyl)imidazo[1,2-c]pyridine-2-carboxamide,
- 6-Chloro-N-(3-chlorophenyl)imidazo[1,2-c]pyridine-2-carboxamide, 6-Chloro-N-(3-methoxyphenyl)imidazo[1,2-c]pyridine-2-carboxamide,
6-Chloro-N[4-(dimethylamino)phenyl]imidazo[1,2-c]pyridine-2-carboxamide,
6-Chloro-N-(4-chlorophenyl)imidazo[1,2-c]pyridine-2-carboxamide,
6-[2-(Hydroxymethyl)phenyl]-N-phenylimidazo[1,2-c]pyridine-2-carboxamide,
6-[3-(Hydroxymethyl)phenyl]-N-phenylimidazo[1,2-c]pyridine-2-carboxamide,
6-[4-(Hydroxymethyl)phenyl]-N-phenylimidazo[1,2-c]pyridine-2-carboxamide,
6-(2-Formylphenyl)-N-phenylimidazo[1,2-c]pyridine-2-carboxamide,
6-(3-Formylphenyl)-N-phenylimidazo[1,2-c]pyridine-2-carboxamide,
5,6-Dimethyl-N-phenylimidazo[1,2-c]pyridine-2-carboxamide,
Methyl 3-[2-(anilinocarbonyl)imidazo[1,2-c]pyridin-6-yl]benzoate,
6-(3-Acetylphenyl)-N-phenylimidazo[1,2-c]pyridine-2-carboxamide,
6-(3-Fluorophenyl)-N-phenylimidazo[1,2-c]pyridine-2-carboxamide,
6-(4-Methylphenyl)-N-phenylimidazo[1,2-c]pyridine-2-carboxamide,
6-(3-Methoxyphenyl)-N-phenylimidazo[1,2-c]pyridine-2-carboxamide,
6-[3-(Aminomethyl)phenyl]-N-phenylimidazo[1,2-c]pyridine-2-carboxamide,
6-(3-Chlorophenyl)-N-phenylimidazo[1,2-c]pyridine-2-carboxamide,
6-(3-Carbamoylphenyl)-N-phenylimidazo[1,2-c]pyridine-2-carboxamide,
6-[3-(1-Hydroxyethyl)phenyl]-N-phenylimidazo[1,2-c]pyridine-2-carboxamide,
6-(3-Methylphenyl)-N-phenylimidazo[1,2-c]pyridine-2-carboxamide,
6-(Diethylamino)-N-phenylimidazo[1,2-c]pyridine-2-carboxamide or its hydrochloride (1:1),
6-[3-(Methylcarbamoyl)phenyl]-N-phenylimidazo[1,2-a]pyridine-2-carboxamide or its hydrochloride (1:1),
6-Carbamoyl-N-phenylimidazo[1,2-a]pyridine-2-carboxamide,
6-(Dimethylamino)-N-(3-fluorophenyl)imidazo[1,2-a]pyridine-2-carboxamide,
N-(2,5-Difluorophenyl)-6-(dimethylamino)imidazo[1,2-a]pyridine-2-carboxamide,
N-(2,3-Difluorophenyl)-6-(dimethylamino)imidazo[1,2-a]pyridine-2-carboxamide,
6-(Dimethylamino)-N-(2-fluorophenyl)imidazo[1,2-a]pyridine-2-carboxamide,
N-(3-Fluorophenyl)-6-[3-(hydroxymethyl)phenyl]imidazo[1,2-a]pyridine-2-carboxamide,
N-(3,5-Difluorophenyl)-6-[3-(hydroxymethyl)phenyl]imidazo[1,2-a]pyridine-2-carboxamide,
N-(2-Chlorophenyl)-6-[3-(hydroxymethyl)phenyl]imidazo[1,2-a]pyridine-2-carboxamide,
6-[3-(Hydroxymethyl)phenyl]-N-(3-methylphenyl)imidazo[1,2-a]pyridine-2-carboxamide,
N-(2,5-Difluorophenyl)-6-[3-(hydroxymethyl)phenyl]imidazo[1,2-a]pyridine-2-carboxamide,
N-(2,3-Difluorophenyl)-6-[3-(hydroxymethyl)phenyl]imidazo[1,2-a]pyridine-2-carboxamide,
N-(2-Fluorophenyl)-6-[3-(hydroxymethyl)phenyl]imidazo[1,2-a]pyridine-2-carboxamide,
N-(5-Chloro-2-fluorophenyl)-6-[3-(hydroxymethyl)phenyl]imidazo[1,2-a]pyridine-2-carboxamide,
6-Morpholin-4-yl-N-phenylimidazo[1,2-a]pyridine-2-carboxamide or its hydrochloride (1:1),
6-Azetidin-1-yl-N-phenylimidazo[1,2-a]pyridine-2-carboxamide,
6-Iodo-5-methyl-N-phenylimidazo[1,2-a]pyridine-2-carboxamide,
N-(3,5-Difluorophenyl)-6-iodoimidazo[1,2-a]pyridine-2-carboxamide,
N-(3-Chlorophenyl)-6-[3-(hydroxymethyl)phenyl]imidazo[1,2-a]pyridine-2-carboxamide,
N-(3,5-Difluorophenyl)-6-(dimethylamino)imidazo[1,2-c]pyridine-2-carboxamide,
N-(2-Chlorophenyl)-6-(dimethylamino)imidazo[1,2-c]pyridine-2-carboxamide,
6-(Dimethylamino)-N[3-(trifluoromethoxy)phenyl]imidazo[1,2-a]pyridine-2-carboxamide,
N-(3-Chloro-2-fluorophenyl)-6-[3-(hydroxymethyl)phenyl]imidazo[1,2-a]pyridine-2-carboxamide,
6-(Dimethylamino)-N-(3-methylphenyl)imidazo[1,2-a]pyridine-2-carboxamide,
N-(3-Chlorophenyl)-6-(dimethylamino)imidazo[1,2-c]pyridine-2-carboxamide,
N-(5-Chloro-2-fluorophenyl)-6-(dimethylamino)imidazo[1,2-c]pyridine-2-carboxamide,
N-(3-Chloro-2-fluorophenyl)-6-(dimethylamino)imidazo[1,2-c]pyridine-2-carboxamide,
N-[3-(Difluoromethoxy)phenyl]-6-(dimethylamino)imidazo[1,2-c]pyridine-2-carboxamide, or
6-(Dimethylamino)-N-[3-(trifluoromethyl)phenyl]imidazo[1,2-c]pyridine-2-carboxamide.

9. A method for treating Alzheimer's disease in a patient in need thereof, comprising administering to the patient a pharmaceutically effective amount of a compound of formula (I) for treating Alzheimer's disease:

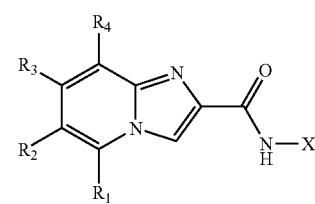

(I)

wherein:
X is phenyl optionally substituted by one or more groups chosen, independently of one another, from the group consisting of halogen, $(C_1-C_6)$alkoxy, $(C_1-C_6)$alkyl, $(C_3-C_7)$cycloalkyl$(C_1-C_6)$alkyl, $(C_3-C_7)$cycloalkyl$(C_1-C_6)$alkoxy, and NRaRb;

$R_1$ is hydrogen, halogen, $(C_1-C_6)$alkoxy, $(C_1-C_6)$alkyl, $(C_3-C_7)$cycloalkyl$(C_1-C_6)$alkyl, $(C_3-C_7)$cycloalkyl$(C_1-C_6)$alkoxy, amino or NRcRd, wherein the alkyl and alkoxy groups are optionally substituted by one or more halogen, hydroxyl, amino, or $(C_1-C_6)$alkoxy;

$R_2$ is hydrogen,
$(C_1-C_6)$alkyl optionally substituted by one or more groups chosen, independently of one another, from the group consisting of hydroxyl, halogen, amino, NRaRb and phenyl,
$(C_1-C_6)$alkoxy optionally substituted by one or more groups chosen, independently of one another, from the group consisting of hydroxyl, halogen, amino, and NRaRb, ($C_3$-$C_7$)cycloalkyl($C_1$-$C_6$)alkyl,
($C_3$-$C_7$)cycloalkyl($C_1$-$C_6$)alkoxy,
($C_2$-$C_6$)alkenyl,
($C_2$-$C_6$)alkynyl,
—CO—$R_5$,
—CO—$NR_6R_7$,
—CO—O—$R_8$,
—$NR_9$—CO—$R_{10}$,
—$NR_{11}R_{12}$,
halogen,
cyano, or
phenyl optionally substituted by one or more groups chosen, independently of one another, from the group consisting of halogen, ($C_1$-$C_6$)alkoxy, NRaRb, —CO—$R_5$, —CO—$NR_6R_7$, —CO—O—$R_8$, ($C_3$-$C_7$)cycloalkyl($C_1$-$C_6$)alkyl, ($C_3$-$C_7$)cycloalkyl-($C_1$-$C_6$)alkoxy, and ($C_1$-$C_6$)alkyl optionally substituted by one or more hydroxyl or NRaRb;

$R_3$ is hydrogen, ($C_1$-$C_6$)alkyl, ($C_1$-$C_6$)alkoxy or halogen;
$R_4$ is hydrogen, ($C_1$-$C_4$)alkyl, ($C_1$-$C_4$)alkoxy or fluorine;
$R_5$ is hydrogen, phenyl or ($C_1$-$C_6$)alkyl;
$R_6$ and $R_7$ are independently hydrogen or ($C_1$-$C_6$)alkyl, or
$R_6$ and $R_7$, taken together with the nitrogen atom to which they are attached, form a 4- to 7-membered ring optionally including another heteroatom chosen from the group consisting of N, O and S;
$R_8$ is ($C_1$-$C_6$)alkyl;
$R_9$ and $R_{10}$ are independently hydrogen or ($C_1$-$C_6$)alkyl;
$R_{11}$ and $R_{12}$ are independently ($C_1$-$C_6$)alkyl, or
$R_{11}$ and $R_{12}$, taken together with the nitrogen atom to which they are attached, form a 4- to 7-membered ring optionally including another heteroatom chosen from the group consisting of N, O and S;
Ra and Rb are independently hydrogen or ($C_1$-$C_6$)alkyl, or
Ra and Rb, taken together with the nitrogen atom to which they are attached, form a 4- to 7-membered ring;
Rc is hydrogen; and
Rd is ($C_1$-$C_6$)alkyl;
provided that:
at least one of $R_1$, $R_2$, $R_3$ and $R_4$ is other than hydrogen,
when $R_3$ is methyl, then X is unsubstituted,
when $R_1$ is methyl, then X is unsubstituted, and
when $R_2$ is chlorine, then X is not a para-fluorophenyl;
or a pharmaceutically acceptable salt thereof.

10. The method according to claim 9, wherein X is phenyl.

11. The method according to claim 9, wherein $R_1$, $R_3$ and $R_4$ are hydrogen.

12. The method according to claim 9, wherein the compound of formula (I) is:

6-Chloro-N-phenylimidazo[1,2-a]pyridine-2-carboxamide,
8-Methyl-N-phenylimidazo[1,2-c]pyridine-2-carboxamide,
6-(Dimethylamino)-N-phenylimidazo[1,2-c]pyridine-2-carboxamide,
6-(1-Hydroxy-1-methylethyl)-N-phenylimidazo[1,2-a]pyridine-2-carboxamide,
N-(4-Fluorophenyl)-6-isopropenylimidazo[1,2-a]pyridine-2-carboxamide,
6-Chloro-N-(2-chlorophenyl)imidazo[1,2-c]pyridine-2-carboxamide,
N,6-Diphenylimidazo[1,2-c]pyridine-2-carboxamide,
N-Phenyl-6-vinylimidazo[1,2-c]pyridine-2-carboxamide,
6-Ethyl-N-phenylimidazo[1,2-c]pyridine-2-carboxamide,
6-Formyl-N-phenylimidazo[1,2-c]pyridine-2-carboxamide,
6-Ethynyl-N-phenylimidazo[1,2-c]pyridine-2-carboxamide,
6-[3-(1-Hydroxy-1-methylethyl)phenyl]-N-phenylimidazo[1,2-c]pyridine-2-carboxamide,
6-[Hydroxy(phenyl)methyl]-N-phenylimidazo[1,2-c]pyridine-2-carboxamide,
6-Acetyl-N-phenylimidazo[1,2-c]pyridine-2-carboxamide hydrochloride (1:1),
6-Isopropyl-N-phenylimidazo[1,2-c]pyridine-2-carboxamide,
6-(1-Hydroxyethyl)-N-phenylimidazo[1,2-c]pyridine-2-carboxamide,
6-Acetamido-N-phenylimidazo[1,2-c]pyridine-2-carboxamide,
6-(Dimethylamino)-5-methyl-N-phenylimidazo[1,2-c]pyridine-2-carboxamide,
6-Methyl-N-phenylimidazo[1,2-c]pyridine-2-carboxamide,
5-Methyl-N-phenylimidazo[1,2-c]pyridine-2-carboxamide,
7-Methyl-N-phenylimidazo[1,2-c]pyridine-2-carboxamide,
6-Bromo-N-phenylimidazo[1,2-c]pyridine-2-carboxamide,
6-Fluoro-N-phenylimidazo[1,2-c]pyridine-2-carboxamide,
6,8-Difluoro-N-phenylimidazo[1,2-c]pyridine-2-carboxamide,
6-Bromo-5-methyl-N-phenylimidazo[1,2-c]pyridine-2-carboxamide,
6-Iodo-N-phenylimidazo[1,2-c]pyridine-2-carboxamide,
6-Cyano-N-phenylimidazo[1,2-c]pyridine-2-carboxamide,
6-(Hydroxymethyl)-N-phenylimidazo[1,2-c]pyridine-2-carboxamide,
6-Methoxy-N-phenylimidazo[1,2-c]pyridine-2-carboxamide,
N-(4-fluorophenyl)-6-(1-hydroxy-1-methylethyl)imidazo[1,2-c]pyridine-2-carboxamide,
6-Benzoyl-N-phenylimidazo[1,2-c]pyridine-2-carboxamide,
6-Isopropenyl-N-phenylimidazo[1,2-c]pyridine-2-carboxamide,
6-Chloro-N-(3-fluorophenyl)imidazo[1,2-c]pyridine-2-carboxamide,
6-Chloro-N-(3-chlorophenyl)imidazo[1,2-c]pyridine-2-carboxamide,
6-Chloro-N-(3-methoxyphenyl)imidazo[1,2-c]pyridine-2-carboxamide,
6-Chloro-N[4-(dimethylamino)phenyl]imidazo[1,2-c]pyridine-2-carboxamide,
6-Chloro-N-(4-chlorophenyl)imidazo[1,2-c]pyridine-2-carboxamide,
6-[2-(Hydroxymethyl)phenyl]-N-phenylimidazo[1,2-c]pyridine-2-carboxamide,
6-[3-(Hydroxymethyl)phenyl]-N-phenylimidazo[1,2-c]pyridine-2-carboxamide,
6-[4-(Hydroxymethyl)phenyl]-N-phenylimidazo[1,2-c]pyridine-2-carboxamide,
6-(2-Formylphenyl)-N-phenylimidazo[1,2-c]pyridine-2-carboxamide,
6-(3-Formylphenyl)-N-phenylimidazo[1,2-c]pyridine-2-carboxamide,
5,6-Dimethyl-N-phenylimidazo[1,2-c]pyridine-2-carboxamide,
Methyl 3-[2-(anilinocarbonyl)imidazo[1,2-c]pyridin-6-yl]benzoate, 6-(3-Acetylphenyl)-N-phenylimidazo[1,2-c]pyridine-2-carboxamide,
6-(3-Fluorophenyl)-N-phenylimidazo[1,2-c]pyridine-2-carboxamide,
6-(4-Methylphenyl)-N-phenylimidazo[1,2-c]pyridine-2-carboxamide,
6-(3-Methoxyphenyl)-N-phenylimidazo[1,2-c]pyridine-2-carboxamide,
6-[3-(Aminomethyl)phenyl]-N-phenylimidazo[1,2-c]pyridine-2-carboxamide,
6-(3-Chlorophenyl)-N-phenylimidazo[1,2-c]pyridine-2-carboxamide,
6-(3-Carbamoylphenyl)-N-phenylimidazo[1,2-c]pyridine-2-carboxamide,
6-[3-(1-Hydroxyethyl)phenyl]-N-phenylimidazo[1,2-c]pyridine-2-carboxamide,
6-(3-Methylphenyl)-N-phenylimidazo[1,2-c]pyridine-2-carboxamide,
6-(Diethylamino)-N-phenylimidazo[1,2-c]pyridine-2-carboxamide or its hydrochloride (1:1),
6-[3-(Methylcarbamoyl)phenyl]-N-phenylimidazo[1,2-c]pyridine-2-carboxamide or its hydrochloride (1:1),
6-Carbamoyl-N-phenylimidazo[1,2-c]pyridine-2-carboxamide,
6-(Dimethylamino)-N-(3-fluorophenyl)imidazo[1,2-c]pyridine-2-carboxamide,
N-(2,5-Difluorophenyl)-6-(dimethylamino)imidazo[1,2-c]pyridine-2-carboxamide,
N-(2,3-Difluorophenyl)-6-(dimethylamino)imidazo[1,2-c]pyridine-2-carboxamide,
6-(Dimethylamino)-N-(2-fluorophenyl)imidazo[1,2-c]pyridine-2-carboxamide,
N-(3-Fluorophenyl)-6-[3-(hydroxymethyl)phenyl]imidazo[1,2-c]pyridine-2-carboxamide,
N-(3,5-Difluorophenyl)-6-[3-(hydroxymethyl)phenyl]imidazo[1,2-c]pyridine-2-carboxamide,
N-(2-Chlorophenyl)-6-[3-(hydroxymethyl)phenyl]imidazo[1,2-c]pyridine-2-carboxamide,
6-[3-(Hydroxymethyl)phenyl]-N-(3-methylphenyl)imidazo[1,2-c]pyridine-2-carboxamide,
N-(2,5-Difluorophenyl)-6-[3-(hydroxymethyl)phenyl]imidazo[1,2-c]pyridine-2-carboxamide,
N-(2,3-Difluorophenyl)-6-[3-(hydroxymethyl)phenyl]imidazo[1,2-c]pyridine-2-carboxamide,
N-(2-Fluorophenyl)-6-[3-(hydroxymethyl)phenyl]imidazo[1,2-c]pyridine-2-carboxamide,
N-(5-Chloro-2-fluorophenyl)-6-[3-(hydroxymethyl)phenyl]imidazo[1,2-a]pyridine-2-carboxamide,
6-Morpholin-4-yl-N-phenylimidazo[1,2-c]pyridine-2-carboxamide or its hydrochloride (1:1),
6-Azetidin-1-yl-N-phenylimidazo[1,2-c]pyridine-2-carboxamide,
6-Iodo-5-methyl-N-phenylimidazo[1,2-c]pyridine-2-carboxamide,
N-(3,5-Difluorophenyl)-6-iodoimidazo[1,2-c]pyridine-2-carboxamide,
N-(3-Chlorophenyl)-6-[3-(hydroxymethyl)phenyl]imidazo[1,2-c]pyridine-2-carboxamide,
N-(3,5-Difluorophenyl)-6-(dimethylamino)imidazo[1,2-c]pyridine-2-carboxamide,
N-(2-Chlorophenyl)-6-(dimethylamino)imidazo[1,2-c]pyridine-2-carboxamide,
6-(Dimethylamino)-N[3-(trifluoromethoxy)phenyl]imidazo[1,2-c]pyridine-2-carboxamide,
N-(3-Chloro-2-fluorophenyl)-6-[3-(hydroxymethyl)phenyl]imidazo[1,2-a]pyridine-2-carboxamide,
6-(Dimethylamino)-N-(3-methylphenyl)imidazo[1,2-c]pyridine-2-carboxamide,
N-(3-Chlorophenyl)-6-(dimethylamino)imidazo[1,2-c]pyridine-2-carboxamide,
N-(5-Chloro-2-fluorophenyl)-6-(dimethylamino)imidazo[1,2-c]pyridine-2-carboxamide,
N-(3-Chloro-2-fluorophenyl)-6-(dimethylamino)imidazo[1,2-c]pyridine-2-carboxamide,
N-[3-(Difluoromethoxy)phenyl]-6-(dimethylamino)imidazo[1,2-c]pyridine-2-carboxamide, or
6-(Dimethylamino)-N-[3-(trifluoromethyl)phenyl]imidazo[1,2-c]pyridine-2-carboxamide.

\* \* \* \* \*